US006214555B1

(12) United States Patent
Leushner et al.

(10) Patent No.: US 6,214,555 B1
(45) Date of Patent: Apr. 10, 2001

(54) METHOD COMPOSITIONS AND KIT FOR DETECTION

(75) Inventors: James Leushner, North York; May Hui, Toronto; James M. Dunn, Scarborough; Jean-Michel LaCroix, Etobicoke, all of (CA)

(73) Assignee: Visible Genetics Inc., Toronto (CA)

( * ) Notice: Subject to any disclaimer, the term of this patent is extended or adjusted under 35 U.S.C. 154(b) by 0 days.

(21) Appl. No.: 09/311,260

(22) Filed: May 13, 1999

Related U.S. Application Data

(63) Continuation-in-part of application No. 09/009,483, filed on Jan. 20, 1998, which is a continuation-in-part of application No. 08/640,672, filed on May 1, 1996, now Pat. No. 5,789,168, which is a continuation-in-part of application No. 08/684,498, filed on Jul. 19, 1996, now Pat. No. 5,830,657, which is a continuation-in-part of application No. 08/807,138, filed on Feb. 22, 1997, now Pat. No. 5,888,736.

(51) Int. Cl.$^7$ .............................. C12Q 1/68; C07K 13/00

(52) U.S. Cl. ............................................. 435/6; 530/350

(58) Field of Search ..................... 435/6, 91.2; 536/22.1; 530/350

(56) References Cited

U.S. PATENT DOCUMENTS

| 4,683,194 | 7/1987 | Saiki et al. ................................ 435/6 |
| 4,683,195 | 7/1987 | Mullis et al. ............................. 435/6 |
| 4,729,947 | 3/1988 | Middendorf et al. ................... 435/6 |
| 4,795,699 | 1/1989 | Tabor et al. .............................. 435/5 |
| 4,889,818 | 12/1989 | Gelfand et al. ....................... 435/194 |
| 4,965,188 | 10/1990 | Mullis et al. ............................. 435/6 |
| 5,079,352 | 1/1992 | Gelfand et al. ........................ 538/27 |
| 5,352,600 | 10/1994 | Gelfand et al. ....................... 435/194 |
| 5,427,911 | 6/1995 | Ruano ...................................... 435/6 |

FOREIGN PATENT DOCUMENTS

| 0265293 | 4/1988 | (EP) . |
| 0386859 | 9/1990 | (EP) . |
| 0655506 | 5/1995 | (EP) . |
| 8907149 | 8/1989 | (WO) . |
| 9302212 | 2/1993 | (WO) . |
| 9308305 | 4/1993 | (WO) . |
| 9426894 | 11/1994 | (WO) . |
| 9601909 | 1/1996 | (WO) . |

OTHER PUBLICATIONS

Murakawa et al., :Direct Detection of HIV–1 RNA from AIDS and ARC Patient Samples *DNA* 7: 287–295 (1988).

Carothers et al., "Point Mutation Analysis in A Mammalian Gene: Rapid Preparation of Total RNA, PCR Amplification of cDNA, and Taq Sequencing by a Novel Method" *BioTechniques* 7: 494–498 (19.

Murray, V., "Improved Double–Stranded DNA Sequencing Using the Linear Polymerase Chain Reaction", *Nucl. Acids Res.* 17: 8889 (1989).

Sanger et al., "DNA Sequencing with Chain–Terminating Inhibitors", *Proc. Nat'l Acad. Sci.* 74: 5463–5467 (1977).

Miller et al, "Chain Terminator Sequencing of Double–Stranded DNA With Built in Error Correction", General Atomics Pre–Print (1991).

Nuovo, G.J., "In situ PCR" in Dieffenbach et al., *PCR Primer: A Laboratory Manual*, pp. 235–248, Cold Spring Harbor Laboratory Press (1995).

Ruano et al., "Coupled Amplification and sequencing of genomic DNA", *Proc. Nat'l Acad. Sci. (USA)* 88: 2815–2819 (1991).

Rao, V. B., "Direct–Sequencing of Polymerase Chain Reaction–Amplified DNA", *Anal Biochem,* 216: 1–14 (1994).

Kretz et al., "Cycle Sequencing" in *PCR Methods and Applications* 3: S107–S112 (1994).

Deng et al., "Simultaneous amplification and sequencing of genomic DNA (SAS) : sequencing of 16S rRNA genes using total genomic DNA from *Butyrovibrio fibrisolvens,* and detection and genotyping of non–cultruable mycoplasma–like organisms directly from total DNA isolated from infected plants", *J. Microbiol. Methods* 17: 103–113 (1993).

Tabor et al., "A single residue in DNA Polymerases of the *Escherichia coli* DNA polymerase I family is critical for distinguishing between deoxy and dideoxynucleotides", *Proc. Nat'l Acad. Sci. USA*.92: 6339–6343 (1995).

Reeve et al., A novel thermostable polymerase for DNA sequencing *Nature* 376: 796–797 (1995).

Kambara et al, "Real Time Automated Simultaneous Double Stranded DNA Sequencing Using Two–Color Fluorophore Labeling" *Biotechnology* 9: 648–651 (1991).

Sarkar et al., "Dideoxy Fingerprinting (ddF): A rapid and Efficient Screen for the Presence of Mutations" *Genomics* 13: 441–443 (1992).

Wiemann et al., "Simultaneous On–Line Sequencing on Both Strands with Two Fluorescent Dyes" *Anal Biochem.* 224: 117–121 (1995).

Gyllenstein et al., "Generation of single–stranded DNA by polymerase chain reaction and its application to direct sequencing of the HLA–DQA locus" *Proc. Nat'l Acad. Sci. USA* 85: 7652–7656 (1988).

(List continued on next page.)

*Primary Examiner*—Eggerton A. Campbell
(74) *Attorney, Agent, or Firm*—Oppedahl & Larson LLP

(57) ABSTRACT

Evaluation of a sample for the presence and qualitative nature of a microorganism can be performed in a single vessel by combining a natural abundance DNA sample with a sequencing mixture containing a primer pair, a thermally stable polymerase such as ThermoSequenase™ which incorporates dideoxynucleotides into an extending nucleic acid polymer at a rate which is no less than about 0.4 times the rate of incorporation of deoxynucleotides, nucleotide triphosphate feedstocks, and a chain terminating nucleotide triphosphate. The mixture is processed through multiple thermal cycles for annealing, extension and denaturation to produce a product mixture which is analyzed by electrophoresis.

12 Claims, No Drawings

OTHER PUBLICATIONS

Mullis et al., "Specific Synthesis of DNA in Vitro via a Polymerase–Catalyzed Chain Reaction" *Meth. Enzymol.* 155: 335–350 (1987).

Ruano et al., "Genotyping and haplotyping of polymorphisms directly from genomic DNA via coupled amplification and sequencing (CAS)" *Nucl. Acids Res.* 19: 6877–6882 (1991).

Wiemann et al., "Simultaneous On–Line DNA Sequencing on Both Strands with Two Fluorescent Dyes", *Anal. Biochem.* 224: 117–121 (1995).

Olesen et al., "Chemiluminescent DNA sequencing with multiplex labeling", *Biotechniques* 15: 480–485 (1993).

Wiemann et al., "Doublex fluorescent DNA sequencing: two independent sequences obtained simultaneously with one reaction with internal labeling an unlabeled primers", *Anal. Biochem* 234: 166–174 (1996).

Creasey et al., "Application of a novel chemiluminescence–based DNA detection method to a single–vector and multiplex DNA sequencing" *Biotechniques* 11: 102–109 (1991).

Roemer et al., "Simultaneous Bi–Directional Cycle Sequencing", Poster presented at $9^{th}$ International Genome Sequencing and Analysis Conference, Hilton Head, SC, Sep. 1997.

SEQUENCE LISTING (1) GENERAL INFORMATION:

(iii) NUMBER OF SEQUENCES: 189

(2) INFORMATION FOR SEQ ID NO: 1:

(i) SEQUENCE CHARACTERISTICS:
      (A) LENGTH: 20
      (B) TYPE: nucleic acid
      (C) STRANDEDNESS: double
      (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
      (A) ORGANISM: Chlamydia trachomatis (ix) FEATURE:
      (D) OTHER INFORMATION: primer for sequencing of cryptic
         plasmid (xi) SEQUENCE DESCRIPTION: SEQ ID NO:1:

TCCGGAGCGA GTTACGAAGA                                            20

(2) INFORMATION FOR SEQ ID NO: 2:

(i) SEQUENCE CHARACTERISTICS:
      (A) LENGTH: 20
      (B) TYPE: nucleic acid
      (C) STRANDEDNESS: double
      (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
      (A) ORGANISM: Chlamydia trachomatis (ix) FEATURE:
      (D) OTHER INFORMATION: primer for sequencing of cryptic plasmid (xi) SEQUENCE DESCRIPTION: SEQ ID NO:2:

ATTCAATGCC CGGGATTGGT                                                      20

(2) INFORMATION FOR SEQ ID NO: 3:

(i) SEQUENCE CHARACTERISTICS:
        (A) LENGTH: 25
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
        (A) ORGANISM: Chlamydia trachomatis (ix) FEATURE:
        (D) OTHER INFORMATION: primer for sequencing of VS regions (xi) SEQUENCE DESCRIPTION: SEQ ID NO:3:

CCGACCGCGT CTTGAAAACA GATGT                                                25

(2) INFORMATION FOR SEQ ID NO: 4:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
        (A) ORGANISM: Chlamydia trachomatis (ix) FEATURE:
        (D) OTHER INFORMATION: primer for sequencing of VS regions (xi) SEQUENCE DESCRIPTION: SEQ ID NO:4:

CACCCACATT CCCAGAGAGC T                                                    21

(2) INFORMATION FOR SEQ ID NO: 5:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
        (A) ORGANISM: Chlamydia trachomatis (ix) FEATURE:
        (D) OTHER INFORMATION: primer for sequencing of VS regions (xi) SEQUENCE DESCRIPTION: SEQ ID NO:5:

CGTGCAGCTT TGTGGGAATG T                                         21

(2) INFORMATION FOR SEQ ID NO: 6:

(i) SEQUENCE CHARACTERISTICS:
        (A) LENGTH: 24
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
        (A) ORGANISM: Chlamydia trachomatis (ix) FEATURE:
        (D) OTHER INFORMATION: primer for sequencing of VS regions (xi) SEQUENCE DESCRIPTION: SEQ ID NO:6:

CTAGATTTCA TCTTGTTCAA TTGC                                      24

(2) INFORMATION FOR SEQ ID NO: 7:

(i) SEQUENCE CHARACTERISTICS:
        (A) LENGTH: 23
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
        (A) ORGANISM: Chlamydia trachomatis (ix) FEATURE:
        (D) OTHER INFORMATION: primer for sequencing of VS regions (xi) SEQUENCE DESCRIPTION: SEQ ID NO:7:

AGCATGCGTR TKGGTTACTA YGG                                       23

(2) INFORMATION FOR SEQ ID NO: 8:

(i) SEQUENCE CHARACTERISTICS:
        (A) LENGTH: 24
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
         (A) ORGANISM: Chlamydia trachomatis (ix) FEATURE:
         (D) OTHER INFORMATION: primer for sequencing of VS regions (xi) SEQUENCE DESCRIPTION: SEQ ID NO:8:

TGACTTTGTT TTCGACCGYG TTTT                                              24

(2) INFORMATION FOR SEQ ID NO: 9:

(i) SEQUENCE CHARACTERISTICS:
         (A) LENGTH: 23
         (B) TYPE: nucleic acid
         (C) STRANDEDNESS: double
         (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
         (A) ORGANISM: Chlamydia trachomatis (ix) FEATURE:
         (D) OTHER INFORMATION: primer for sequencing of VS regions (xi) SEQUENCE DESCRIPTION: SEQ ID NO:9:

CTAAAGTYGC RCATCCACAT TCC                                               23

(2) INFORMATION FOR SEQ ID NO: 10:

(i) SEQUENCE CHARACTERISTICS:
         (A) LENGTH: 23
         (B) TYPE: nucleic acid
         (C) STRANDEDNESS: double
         (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
         (A) ORGANISM: Chlamydia trachomatis (ix) FEATURE:
         (D) OTHER INFORMATION: primer for sequencing of VS regions (xi) SEQUENCE DESCRIPTION: SEQ ID NO:10:

CATCCACATT CCCASARAGC TGC                                               23

(2) INFORMATION FOR SEQ ID NO: 11:

(i) SEQUENCE CHARACTERISTICS:
         (A) LENGTH: 20
         (B) TYPE: nucleic acid
         (C) STRANDEDNESS: double
         (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
            (A) ORGANISM: Chlamydia trachomatis (ix) FEATURE:
            (D) OTHER INFORMATION: primer for sequencing of cryptic
                plasmid (xi) SEQUENCE DESCRIPTION: SEQ ID NO:11:

ATGCCCGGGA TTGGTTGATC                                              20

(2) INFORMATION FOR SEQ ID NO: 12:

(i) SEQUENCE CHARACTERISTICS:
            (A) LENGTH: 20
            (B) TYPE: nucleic acid
            (C) STRANDEDNESS: double
            (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
            (A) ORGANISM: Chlamydia trachomatis (ix) FEATURE:
            (D) OTHER INFORMATION: primer for sequencing of VS regions (xi) SEQUENCE DESCRIPTION: SEQ ID NO:12:

GGAGACTTTG TTTTCGACCG                                              20

(2) INFORMATION FOR SEQ ID NO: 13:

(i) SEQUENCE CHARACTERISTICS:
            (A) LENGTH: 20
            (B) TYPE: nucleic acid
            (C) STRANDEDNESS: double
            (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
            (A) ORGANISM: Chlamydia trachomatis (ix) FEATURE:
            (D) OTHER INFORMATION: primer for sequencing of VS regions (xi) SEQUENCE DESCRIPTION: SEQ ID NO:13:

CATTCCCACA AAGCTGCGCG                                              20

(2) INFORMATION FOR SEQ ID NO: 14:

(i) SEQUENCE CHARACTERISTICS:
            (A) LENGTH: 20
            (B) TYPE: nucleic acid
            (C) STRANDEDNESS: double
            (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
            (A) ORGANISM: Chlamydia trachomatis (ix) FEATURE:
            (D) OTHER INFORMATION: primer for sequencing of VS regions (xi) SEQUENCE DESCRIPTION: SEQ ID NO:14:

TTCCCACAAA GCTGCGCGAG                                                    20

(2) INFORMATION FOR SEQ ID NO: 15:

(i) SEQUENCE CHARACTERISTICS:
            (A) LENGTH: 20
            (B) TYPE: nucleic acid
            (C) STRANDEDNESS: double
            (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
            (A) ORGANISM: Chlamydia trachomatis (ix) FEATURE:
            (D) OTHER INFORMATION: primer for sequencing of VS regions (xi) SEQUENCE DESCRIPTION: SEQ ID NO:15:

CCCACAAAGC TGCGCGAGCG                                                    20

(2) INFORMATION FOR SEQ ID NO: 16:

(i) SEQUENCE CHARACTERISTICS:
            (A) LENGTH: 24
            (B) TYPE: nucleic acid
            (C) STRANDEDNESS: double
            (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
            (A) ORGANISM: Chlamydia trachomatis (ix) FEATURE:
            (D) OTHER INFORMATION: primer for sequencing of ribosomal DNA (xi) SEQUENCE DESCRIPTION: SEQ ID NO: 16:

ACCTTTCGGT TGAGGGAGAG TCTA                                               24

(2) INFORMATION FOR SEQ ID NO: 17:

(i) SEQUENCE CHARACTERISTICS:
            (A) LENGTH: 24
            (B) TYPE: nucleic acid
            (C) STRANDEDNESS: double
            (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
             (A) ORGANISM: Chlamydia trachomatis (ix) FEATURE:
             (D) OTHER INFORMATION: primer for sequencing of ribosomal DNA (xi) SEQUENCE DESCRIPTION: SEQ ID NO:17:

GGACCAATTC TTATTCCCAA GCGA                                              24

(2) INFORMATION FOR SEQ ID NO: 18:

(i) SEQUENCE CHARACTERISTICS:
             (A) LENGTH: 20
             (B) TYPE: nucleic acid
             (C) STRANDEDNESS: double
             (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
             (A) ORGANISM: HIV-1

(ix) FEATURE:
             (D) OTHER INFORMATION: primer for sequencing of HIV-1 protease
                 gene (xi) SEQUENCE DESCRIPTION: SEQ ID NO:18:

ATCACTCTTT GGCAACGACC                                                   20

(2) INFORMATION FOR SEQ ID NO: 19:

(i) SEQUENCE CHARACTERISTICS:
             (A) LENGTH: 24
             (B) TYPE: nucleic acid
             (C) STRANDEDNESS: double
             (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
             (A) ORGANISM: HIV-1

(ix) FEATURE:
             (D) OTHER INFORMATION: primer for sequencing of HIV-1 protease
                 gene (xi) SEQUENCE DESCRIPTION: SEQ ID NO:19:

CAGGAGCAGA TGATACAGTA TTAG                                              24

(2) INFORMATION FOR SEQ ID NO: 20:

(i) SEQUENCE CHARACTERISTICS:
             (A) LENGTH: 25
             (B) TYPE: nucleic acid (C) STRANDEDNESS: double
        (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
        (A) ORGANISM: HIV-1

(ix) FEATURE:
        (D) OTHER INFORMATION: primer for sequencing of HIV-1 protease
            gene (xi) SEQUENCE DESCRIPTION: SEQ ID NO:20:

CCATTCCTGG CTTTAATTTT ACTGG                                           25

(2) INFORMATION FOR SEQ ID NO: 21:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
        (A) ORGANISM: Human Papillomavirus (ix) FEATURE:
        (D) OTHER INFORMATION: primer for sequencing of HPV (xi) SEQUENCE DESCRIPTION: SEQ ID NO:21:

GCMCAGGGWC ATAAYAATGG                                                 20

(2) INFORMATION FOR SEQ ID NO: 22:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
        (A) ORGANISM: Human Papillomavirus (ix) FEATURE:
        (D) OTHER INFORMATION: primer for sequencing of HPV (xi) SEQUENCE DESCRIPTION: SEQ ID NO:22:

CGTCCMAARG GAWACTGATC                                                 20

(2) INFORMATION FOR SEQ ID NO: 23:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:23:

TCAAAKGAAT TGACGGGGGC                                              20

(2) INFORMATION FOR SEQ ID NO: 24:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:24:

AGGCCCGGGA ACGTATTCAC                                              20

(2) INFORMATION FOR SEQ ID NO: 25:

(i) SEQUENCE CHARACTERISTICS:
        (A) LENGTH: 18
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:25:

TGCCAGCAGC CGCGGTAA                                                18

(2) INFORMATION FOR SEQ ID NO: 26:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:26:

```
GGACTACCAG GGTATCTAAT                                                        20
```

(2) INFORMATION FOR SEQ ID NO: 27:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:27:

```
GAGGAAGGTG GGGATGACGT                                                        20
```

(2) INFORMATION FOR SEQ ID NO: 28:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:28:

```
AGGCCCGGGA ACGTATTCAC                                                        20
```

(2) INFORMATION FOR SEQ ID NO: 29:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:29:

```
GAGAGTTTGA TCCTGGCTCA G                                                      21
```

(2) INFORMATION FOR SEQ ID NO: 30:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:30:

CCCACTGCTG CCTCCCGTAG                                                          20

(2) INFORMATION FOR SEQ ID NO: 31:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:31:

GAGAGTTTGA TCCTGGCTCA G                                                        21

(2) INFORMATION FOR SEQ ID NO: 32:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:32:

TTTCACGAAC AACGCGACAA                                                          20

(2) INFORMATION FOR SEQ ID NO: 33:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:33:

CTCGTCCAGC GCCGCTTCGG                                                          20

(2) INFORMATION FOR SEQ ID NO: 34:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:34:

CCTGCGAGCG TAGGCGTCGG                                                    20

(2) INFORMATION FOR SEQ ID NO: 35:

(i) SEQUENCE CHARACTERISTICS:
            (A) LENGTH: 18
            (B) TYPE: nucleic acid
            (C) STRANDEDNESS: double
            (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:35:

TTCTCAATTC GGTAAGGC                                                      18

(2) INFORMATION FOR SEQ ID NO: 36:

(i) SEQUENCE CHARACTERISTICS:
            (A) LENGTH: 20
            (B) TYPE: nucleic acid
            (C) STRANDEDNESS: double
            (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:36:

ATATTGACCA GTGCTATTTC                                                    20

(2) INFORMATION FOR SEQ ID NO: 37:

(i) SEQUENCE CHARACTERISTICS:
            (A) LENGTH: 29
            (B) TYPE: nucleic acid
            (C) STRANDEDNESS: double
            (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:37:

CAATTGCTTA TAACCTTTTG GTTATAAAT                                          29

(2) INFORMATION FOR SEQ ID NO: 38:

(i) SEQUENCE CHARACTERISTICS:

```
        (A) LENGTH: 27
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:38:

TATAGGTACC GTCATTATCT TCCCTAT                                              27

(2) INFORMATION FOR SEQ ID NO: 39:

(i) SEQUENCE CHARACTERISTICS:
        (A) LENGTH: 25
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:39:

TTATGAAAAA ATATTTATTG GGAAT                                                25

(2) INFORMATION FOR SEQ ID NO: 40:

(i) SEQUENCE CHARACTERISTICS:
        (A) LENGTH: 25
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:40:

CTTTAAGCTC AAGCTTGTCT ACTGT                                                25

(2) INFORMATION FOR SEQ ID NO: 41:

(i) SEQUENCE CHARACTERISTICS:
        (A) LENGTH: 25
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:41:

CTGCAGCTTG GAATTCAGGC ACTTC                                                25
```

(2) INFORMATION FOR SEQ ID NO: 42:

(i) SEQUENCE CHARACTERISTICS:
        (A) LENGTH: 24
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:42:

GTTTTGTAAT TTCAACTGCT GACC                                                24

(2) INFORMATION FOR SEQ ID NO: 43:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:43:

ATCTGTTACC AGCATGTAAT                                                      20

(2) INFORMATION FOR SEQ ID NO: 44:

(i) SEQUENCE CHARACTERISTICS:
        (A) LENGTH: 18
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:44:

CCCTCACTAA ACATACCT                                                        18

(2) INFORMATION FOR SEQ ID NO: 45:

(i) SEQUENCE CHARACTERISTICS:
        (A) LENGTH: 29
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:45:

GATGATGCTG CTGGCATGGG AGTTTCTGG                                              29

(2) INFORMATION FOR SEQ ID NO: 46:

(i) SEQUENCE CHARACTERISTICS:
        (A) LENGTH: 31
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO: 46:

CTGTCTGCAT CTGAATATGT GCCGTTACCT G                                           31

(2) INFORMATION FOR SEQ ID NO: 47:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:47:

ATCTTACTTT CCGTGAGAAG                                                        20

(2) INFORMATION FOR SEQ ID NO: 48:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:48:

CTTGGATGTT GAGCTTCCTA                                                        20

(2) INFORMATION FOR SEQ ID NO: 49:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:49:

TTGTGGTAGA CACGGTGGGT AC                                              22

(2) INFORMATION FOR SEQ ID NO: 50:

(i) SEQUENCE CHARACTERISTICS:
    (A) LENGTH: 22
    (B) TYPE: nucleic acid
    (C) STRANDEDNESS: double
    (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:50:

TGATCGCTGA CAAGCTTAGG CT                                              22

(2) INFORMATION FOR SEQ ID NO: 51:

(i) SEQUENCE CHARACTERISTICS:
    (A) LENGTH: 24
    (B) TYPE: nucleic acid
    (C) STRANDEDNESS: double
    (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:51:

CTCAGAGATG AGCCTGCGAC CATT                                            24

(2) INFORMATION FOR SEQ ID NO: 52:

(i) SEQUENCE CHARACTERISTICS:
    (A) LENGTH: 25
    (B) TYPE: nucleic acid
    (C) STRANDEDNESS: double
    (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:52:

GCATTCCCTC CCGTCCTCAT TCTTC                                           25

(2) INFORMATION FOR SEQ ID NO: 53:

(i) SEQUENCE CHARACTERISTICS:
    (A) LENGTH: 24

(B) TYPE: nucleic acid
    (C) STRANDEDNESS: double
    (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:53:

GATAGCGAGC ACAAAGAGAG CTAA                                                24

(2) INFORMATION FOR SEQ ID NO: 54:

(i) SEQUENCE CHARACTERISTICS:
        (A) LENGTH: 36
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:54:

TTCACATCTG TTTGCAAAAC ACGGTCGAAA ACAAAG                                    36

(2) INFORMATION FOR SEQ ID NO: 55:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:55:

GTTGTTCATG AAGGCCTACT                                                     20

(2) INFORMATION FOR SEQ ID NO: 56:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:56:

TGCATAACCT ACGGTGTGTT                                                     20

(2) INFORMATION FOR SEQ ID NO: 57:

(i) SEQUENCE CHARACTERISTICS:
       (A) LENGTH: 21
       (B) TYPE: nucleic acid
       (C) STRANDEDNESS: double
       (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:57:

GAAGCTTATG GTACAGGTTG G                                              21

(2) INFORMATION FOR SEQ ID NO: 58:

(i) SEQUENCE CHARACTERISTICS:
       (A) LENGTH: 20
       (B) TYPE: nucleic acid
       (C) STRANDEDNESS: double
       (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:58:

ATTACCATCC TTGTTGTAAG                                                20

(2) INFORMATION FOR SEQ ID NO: 59:

(i) SEQUENCE CHARACTERISTICS:
       (A) LENGTH: 21
       (B) TYPE: nucleic acid
       (C) STRANDEDNESS: double
       (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:59:

GGCGAATGGG TGAGTAACAC G                                              21

(2) INFORMATION FOR SEQ ID NO: 60:

(i) SEQUENCE CHARACTERISTICS:
       (A) LENGTH: 22
       (B) TYPE: nucleic acid
       (C) STRANDEDNESS: double
       (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:60:

CGGATAACGC TTGCGACCTA TG                                              22

(2) INFORMATION FOR SEQ ID NO: 61:

(i) SEQUENCE CHARACTERISTICS:
        (A) LENGTH: 19
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:61:

GCTATGAGGA ATCTCGCTG                                                  19

(2) INFORMATION FOR SEQ ID NO: 62:

(i) SEQUENCE CHARACTERISTICS:
        (A) LENGTH: 19
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:62:

CTGGCTTCTT CCAGCTTCA                                                  19

(2) INFORMATION FOR SEQ ID NO: 63:

(i) SEQUENCE CHARACTERISTICS:
        (A) LENGTH: 19
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:63:

ATACACGTGG TGGAGGTAC                                                  19

(2) INFORMATION FOR SEQ ID NO: 64:

(i) SEQUENCE CHARACTERISTICS:
        (A) LENGTH: 19
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:64:

GCGGGCAATA TCTTGCATC                                                        19

(2) INFORMATION FOR SEQ ID NO: 65:

(i) SEQUENCE CHARACTERISTICS:
            (A) LENGTH: 24
            (B) TYPE: nucleic acid
            (C) STRANDEDNESS: double
            (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:65:

GGTTATTCGA TTTCTAAATC GCCT                                                  24

(2) INFORMATION FOR SEQ ID NO: 66:

(i) SEQUENCE CHARACTERISTICS:
            (A) LENGTH: 24
            (B) TYPE: nucleic acid
            (C) STRANDEDNESS: double
            (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:66:

GGACTATTGT CTAAACAATT TCCC                                                  24

(2) INFORMATION FOR SEQ ID NO: 67:

(i) SEQUENCE CHARACTERISTICS:
            (A) LENGTH: 18
            (B) TYPE: nucleic acid
            (C) STRANDEDNESS: double
            (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:67:

AGTTTGATCA TGGCTCAG                                                         18

(2) INFORMATION FOR SEQ ID NO: 68:

(i) SEQUENCE CHARACTERISTICS:
            (A) LENGTH: 21
            (B) TYPE: nucleic acid

```
        (C) STRANDEDNESS: double
        (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:68:

GAGTTTGCCG GGACTTCTTC T                                              21

(2) INFORMATION FOR SEQ ID NO: 69:

(i) SEQUENCE CHARACTERISTICS:
        (A) LENGTH: 30
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:69:

AGTTGGAGGA CATCAAGCAG CCATGCAAAT                                     30

(2) INFORMATION FOR SEQ ID NO: 70:

(i) SEQUENCE CHARACTERISTICS:
        (A) LENGTH: 27
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:70:

TGCTATGTCA GTTCCCCTTG GTTCTCT                                        27

(2) INFORMATION FOR SEQ ID NO: 71:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:71:

CCCGGGCCCC CTGACTTGTC                                                20
```

(2) INFORMATION FOR SEQ ID NO: 72:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:72:

GCTTTCACTG TCCCACAGCA G                              21

(2) INFORMATION FOR SEQ ID NO: 73:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:73:

CAAGGTATGT TGCCCGTTTG                              20

(2) INFORMATION FOR SEQ ID NO: 74:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:74:

AAAGCCCTGC GAACCACTGA                              20

(2) INFORMATION FOR SEQ ID NO: 75:

(i) SEQUENCE CHARACTERISTICS:
        (A) LENGTH: 19
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: yes (v) FRAGMENT TYPE: internal

```
        (xi) SEQUENCE DESCRIPTION: SEQ ID NO:75:

CCCAACACTA CTCGGCTAG                                                       19

(2) INFORMATION FOR SEQ ID NO: 76:

(i) SEQUENCE CHARACTERISTICS:
           (A) LENGTH: 24
           (B) TYPE: nucleic acid
           (C) STRANDEDNESS: double
           (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:76:

AACTACTGTC TTCACGCAGA AAGC                                                 24

(2) INFORMATION FOR SEQ ID NO: 77:

(i) SEQUENCE CHARACTERISTICS:
           (A) LENGTH: 22
           (B) TYPE: nucleic acid
           (C) STRANDEDNESS: double
           (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:77:

TACATCGGCG TCATCTGCGG GG                                                   22

(2) INFORMATION FOR SEQ ID NO: 78:

(i) SEQUENCE CHARACTERISTICS:
           (A) LENGTH: 22
           (B) TYPE: nucleic acid
           (C) STRANDEDNESS: double
           (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:78:

CAGTTCGGCG GTGAGGACAA AG                                                   22

(2) INFORMATION FOR SEQ ID NO: 79:

(i) SEQUENCE CHARACTERISTICS:
           (A) LENGTH: 25
           (B) TYPE: nucleic acid
           (C) STRANDEDNESS: double
           (D) TOPOLOGY: linear (ii) MOLECULE TYPE: other nucleic acid (iii) HYPOTHETICAL: no
```

(iv) ANTI-SENSE: yes (v) FRAGMENT TYPE: internal (xi) SEQUENCE DESCRIPTION: SEQ ID NO:79:

AAGCTTGCAC AATGCCAAAA AACAG                                                       25

(2) INFORMATION FOR SEQ ID NO: 80:

(i) SEQUENCE CHARACTERISTICS:
        (A) LENGTH: 25
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:80:

CTCGAGTATG CCGAGACCCC TAATC                                                       25

(2) INFORMATION FOR SEQ ID NO: 81:

(i) SEQUENCE CHARACTERISTICS:
        (A) LENGTH: 26
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:81:

TATCCCAGCT GTTTTCATAT AGTAAC                                                      26

(2) INFORMATION FOR SEQ ID NO: 82:

(i) SEQUENCE CHARACTERISTICS:
        (A) LENGTH: 26
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:82:

GCCTTGCGGT AGCACTAGAT TTTTTG                                                      26

(2) INFORMATION FOR SEQ ID NO: 83:

(i) SEQUENCE CHARACTERISTICS:
        (A) LENGTH: 20
        (B) TYPE: nucleic acid
        (C) STRANDEDNESS: double (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:83:

AAGGATGCCT GGACACAAGA                                               20

(2) INFORMATION FOR SEQ ID NO: 84:

(i) SEQUENCE CHARACTERISTICS:
            (A) LENGTH: 22
            (B) TYPE: nucleic acid
            (C) STRANDEDNESS: double
            (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:84:

TGGTGCTGCT GGTGGTGGCA AT                                            22

(2) INFORMATION FOR SEQ ID NO: 85:

(i) SEQUENCE CHARACTERISTICS:
            (A) LENGTH: 25
            (B) TYPE: nucleic acid
            (C) STRANDEDNESS: double
            (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:85:

CCTAGTGTGG ATGACCTACG GGCCA                                         25

(2) INFORMATION FOR SEQ ID NO: 86:

(i) SEQUENCE CHARACTERISTICS:
            (A) LENGTH: 25
            (B) TYPE: nucleic acid
            (C) STRANDEDNESS: double
            (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:86:

CAGACACAGT GTCCTCCCGC TCCTC                                         25

(2) INFORMATION FOR SEQ ID NO: 87:

```
    (i) SEQUENCE CHARACTERISTICS:
         (A) LENGTH: 20
         (B) TYPE: nucleic acid
         (C) STRANDEDNESS: double
         (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:87:

ATGTCCGTAC AACATCAACT                                                       20

(2) INFORMATION FOR SEQ ID NO: 88:

(i) SEQUENCE CHARACTERISTICS:
         (A) LENGTH: 20
         (B) TYPE: nucleic acid
         (C) STRANDEDNESS: double
         (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:88:

CGATTTTCCA AGAGAGACGC                                                       20

(2) INFORMATION FOR SEQ ID NO: 89:

(i) SEQUENCE CHARACTERISTICS:
         (A) LENGTH: 20
         (B) TYPE: nucleic acid
         (C) STRANDEDNESS: double
         (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:89:

AGTCTTTAGG GTCTTCTACC                                                       20

(2) INFORMATION FOR SEQ ID NO: 90:

(i) SEQUENCE CHARACTERISTICS:
         (A) LENGTH: 20
         (B) TYPE: nucleic acid
         (C) STRANDEDNESS: double
         (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:90:
```

GGTGCCAACC TATGGAACAG                                              20

(2) INFORMATION FOR SEQ ID NO: 91:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:91:

GGAACAGACT TAGAGCTTAT TC                                           22

(2) INFORMATION FOR SEQ ID NO: 92:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:92:

GCTTGTGTAA GTCTTCACTA G                                            21

(2) INFORMATION FOR SEQ ID NO: 93:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:93:

CAATAGCTGG TTTTATAGAA                                              20

(2) INFORMATION FOR SEQ ID NO: 94:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:94:

TTATCATACA GATTCTTGAC                                                               20

(2) INFORMATION FOR SEQ ID NO: 95:

(i) SEQUENCE CHARACTERISTICS:
            (A) LENGTH: 20
            (B) TYPE: nucleic acid
            (C) STRANDEDNESS: double
            (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:95:

GAAGGCAAAG CAGAACTAGC                                                               20

(2) INFORMATION FOR SEQ ID NO: 96:

(i) SEQUENCE CHARACTERISTICS:
            (A) LENGTH: 20
            (B) TYPE: nucleic acid
            (C) STRANDEDNESS: double
            (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:96:

TGGCCTTCTG CTATTTCAAA                                                               20

(2) INFORMATION FOR SEQ ID NO: 97:

(i) SEQUENCE CHARACTERISTICS:
            (A) LENGTH: 20
            (B) TYPE: nucleic acid
            (C) STRANDEDNESS: double
            (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:97:

GTGCAAACTG CATCTTGTGG                                                               20

(2) INFORMATION FOR SEQ ID NO: 98:

(i) SEQUENCE CHARACTERISTICS:
            (A) LENGTH: 20
            (B) TYPE: nucleic acid
            (C) STRANDEDNESS: double
            (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:98:

CTCATTTCTT GATCTCCATG                                                  20

(2) INFORMATION FOR SEQ ID NO: 99:

(i) SEQUENCE CHARACTERISTICS:
            (A) LENGTH: 20
            (B) TYPE: nucleic acid
            (C) STRANDEDNESS: double
            (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:99:

GGACCAAGAG AAAACGTAGC                                                  20

(2) INFORMATION FOR SEQ ID NO: 100:

(i) SEQUENCE CHARACTERISTICS:
            (A) LENGTH: 27
            (B) TYPE: nucleic acid
            (C) STRANDEDNESS: double
            (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:100:

GGTCACATCA TACAATTCTA ATCTAAG                                          27

(2) INFORMATION FOR SEQ ID NO: 101:

(i) SEQUENCE CHARACTERISTICS:
            (A) LENGTH: 26
            (B) TYPE: nucleic acid
            (C) STRANDEDNESS: double
            (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:101:

ATGACTTTTG AGGTGGATCC CATGGA                                           26

(2) INFORMATION FOR SEQ ID NO: 102:

(i) SEQUENCE CHARACTERISTICS:
            (A) LENGTH: 23
            (B) TYPE: nucleic acid
            (C) STRANDEDNESS: double
            (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:102:

GCCGAGAAGG GCGTGCGCAG GTA                                                  23

(2) INFORMATION FOR SEQ ID NO: 103:

(i) SEQUENCE CHARACTERISTICS:
            (A) LENGTH: 24
            (B) TYPE: nucleic acid
            (C) STRANDEDNESS: double
            (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO: 103:

TGCTTTGCCC CATGGGACCT CGAG                                                 24

(2) INFORMATION FOR SEQ ID NO: 104:

(i) SEQUENCE CHARACTERISTICS:
            (A) LENGTH: 21
            (B) TYPE: nucleic acid
            (C) STRANDEDNESS: double
            (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:104:

GGCGAACACG CTCATCACGG T                                                    21

(2) INFORMATION FOR SEQ ID NO: 105:

(i) SEQUENCE CHARACTERISTICS:
            (A) LENGTH: 25
            (B) TYPE: nucleic acid
            (C) STRANDEDNESS: double
            (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:105:

CCTCCGGCCC CTGAATGCGG CTAAT                                           25

(2) INFORMATION FOR SEQ ID NO: 106:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:106:

ATTGTCACCA TAAGCAGCCA                                                 20

(2) INFORMATION FOR SEQ ID NO: 107:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:107:

GCMCAGGGWC ATAAYAATGG                                                 20

(2) INFORMATION FOR SEQ ID NO: 108:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO: 108:

CGTCCMAARG GAWACTGATC                                                 20

(2) INFORMATION FOR SEQ ID NO: 109:

(i) SEQUENCE CHARACTERISTICS:
        (A) LENGTH: 26
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:109:

CACTGAATAA GAGGATACAA GAATGG                                            26

(2) INFORMATION FOR SEQ ID NO: 110:

(i) SEQUENCE CHARACTERISTICS:
            (A) LENGTH: 23
            (B) TYPE: nucleic acid
            (C) STRANDEDNESS: double
            (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:110:

GGAGGAATAT TACATGTGCC TTT                                               23

(2) INFORMATION FOR SEQ ID NO: 111:

(i) SEQUENCE CHARACTERISTICS:
            (A) LENGTH: 19
            (B) TYPE: nucleic acid
            (C) STRANDEDNESS: double
            (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:111:

TCCGTAGGTG AACCTGCGA                                                    19

(2) INFORMATION FOR SEQ ID NO: 112:

(i) SEQUENCE CHARACTERISTICS:
            (A) LENGTH: 20
            (B) TYPE: nucleic acid
            (C) STRANDEDNESS: double
            (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:112:

TCCTCCGCTT ATTGATATGC                                                   20

(2) INFORMATION FOR SEQ ID NO: 113:

(i) SEQUENCE CHARACTERISTICS:
            (A) LENGTH: 20
            (B) TYPE: nucleic acid
            (C) STRANDEDNESS: double
            (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:113:

AGTTACGGCC ATACCTCAGA                                              20

(2) INFORMATION FOR SEQ ID NO: 114:

(i) SEQUENCE CHARACTERISTICS:
            (A) LENGTH: 20
            (B) TYPE: nucleic acid
            (C) STRANDEDNESS: double
            (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:114:

AAAGCTACAG CACGTCGTAT                                              20

(2) INFORMATION FOR SEQ ID NO: 115:

(i) SEQUENCE CHARACTERISTICS:
            (A) LENGTH: 21
            (B) TYPE: nucleic acid
            (C) STRANDEDNESS: double
            (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:115:

GCAAGTCTGG TGCCAGCAGC C                                            21

(2) INFORMATION FOR SEQ ID NO: 116:

(i) SEQUENCE CHARACTERISTICS:
            (A) LENGTH: 27
            (B) TYPE: nucleic acid
            (C) STRANDEDNESS: double
            (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:116:

CCGTCAATTC CTTTATGTTT CAGCCTT                                      27

(2) INFORMATION FOR SEQ ID NO: 117:

(i) SEQUENCE CHARACTERISTICS:

(A) LENGTH: 26
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:117:

AAATAATGKA CGGGTGAGAT GCATGA                                              26

(2) INFORMATION FOR SEQ ID NO: 118:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:118:

GGGTTCGATT GGGGTTGGTG T                                                   21

(2) INFORMATION FOR SEQ ID NO: 119:

(i) SEQUENCE CHARACTERISTICS:
        (A) LENGTH: 18
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:119:

GTGGGGGAGG GGCGTTCT                                                       18

(2) INFORMATION FOR SEQ ID NO: 120:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:120:

ATTTTACACC AACCCCCAGT T                                                   21

(2) INFORMATION FOR SEQ ID NO: 121:

(i) SEQUENCE CHARACTERISTICS:
        (A) LENGTH: 24
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:121:

GGATAACTAC GGAAAAGCTG TAGC                                          24

(2) INFORMATION FOR SEQ ID NO: 122:

(i) SEQUENCE CHARACTERISTICS:
        (A) LENGTH: 27
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO: 122:

CGACTTCTCC TTCCTTTAAA AGATAGG                                       27

(2) INFORMATION FOR SEQ ID NO: 123:

(i) SEQUENCE CHARACTERISTICS:
        (A) LENGTH: 32
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: no (v) FRAGMENT TYPE: internal (ix) FEATURE:
        (D) OTHER INFORMATION: Maximum fragment size: about 500 nt (xi) SEQUENCE DESCRIPTION: SEQ ID NO:123:

GTTCAAGATT AATAATTGCA ATAATCTATC CC                                 32

(2) INFORMATION FOR SEQ ID NO: 124:

(i) SEQUENCE CHARACTERISTICS:
        (A) LENGTH: 24
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:124:

GGCCAATTCA TTCAATGAAT TGAG                                           24

(2) INFORMATION FOR SEQ ID NO: 125:

(i) SEQUENCE CHARACTERISTICS:
             (A) LENGTH: 25
             (B) TYPE: nucleic acid
             (C) STRANDEDNESS: double
             (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:125:

CTCAGATCTA GAAACAATGC TTCTC                                          25

(2) INFORMATION FOR SEQ ID NO: 126:

(i) SEQUENCE CHARACTERISTICS:
             (A) LENGTH: 23
             (B) TYPE: nucleic acid
             (C) STRANDEDNESS: double
             (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:126:

CTTAGTATAA GCTTTTATAC AGC                                            23

(2) INFORMATION FOR SEQ ID NO: 127:

(i) SEQUENCE CHARACTERISTICS:
             (A) LENGTH: 25
             (B) TYPE: nucleic acid
             (C) STRANDEDNESS: double
             (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO: 127:

ATAGGTCAGA AACTTGAATG ATACA                                          25

(2) INFORMATION FOR SEQ ID NO: 128:

(i) SEQUENCE CHARACTERISTICS:
             (A) LENGTH: 20
             (B) TYPE: nucleic acid
             (C) STRANDEDNESS: double (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:128:

GCGCACCAGG AATGTCTTGT                                               20

(2) INFORMATION FOR SEQ ID NO: 129:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:129:

TCACCTACGG ATACCTTGTT                                               20

(2) INFORMATION FOR SEQ ID NO: 130:

(i) SEQUENCE CHARACTERISTICS:
        (A) LENGTH: 26
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:130:

CCGAGTTTGA TCCAAAAAGT TACGAA       26

(2) INFORMATION FOR SEQ ID NO: 131:

(i) SEQUENCE CHARACTERISTICS:
        (A) LENGTH: 26
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:131:

TAGCTCCTCA TATGCCTTAT TGAGTA                                        26

(2) INFORMATION FOR SEQ ID NO: 132:

(i) SEQUENCE CHARACTERISTICS:
        (A) LENGTH: 26
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:132:

GGAATTCCTT CCGAGCTTCG CTGCGT                                              26

(2) INFORMATION FOR SEQ ID NO: 133:

(i) SEQUENCE CHARACTERISTICS:
        (A) LENGTH: 28
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:133:

CGGGATCCCG TCTTCAAACC CCCTACTG                                            28

(2) INFORMATION FOR SEQ ID NO: 134:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:134:

CGGGCAGATT CTAGACCTCC TG                                                  22

(2) INFORMATION FOR SEQ ID NO: 135:

(i) SEQUENCE CHARACTERISTICS:
        (A) LENGTH: 23
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:135:

```
CGATGATCTT GGAGCATTCC CAC                                              23

(2) INFORMATION FOR SEQ ID NO: 136:

(i) SEQUENCE CHARACTERISTICS:
        (A) LENGTH: 26
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:136:

CTTGACTCTT CAAAAGAGAA AATTAC                                           26

(2) INFORMATION FOR SEQ ID NO: 137:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:137:

TCTCTATRTG CAYACGGAGC                                                  20

(2) INFORMATION FOR SEQ ID NO: 138:

(i) SEQUENCE CHARACTERISTICS:
        (A) LENGTH: 19
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO: 138:

CCATACTGAT TGCCGCAAT                                                   19

(2) INFORMATION FOR SEQ ID NO: 139:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE: other nucleic acid (iii) HYPOTHETICAL: no
```

(iv) ANTI-SENSE: yes (v) FRAGMENT TYPE: internal (xi) SEQUENCE DESCRIPTION: SEQ ID NO:139:

CTTCGGTATC CTATTCCCGG                                                        20

(2) INFORMATION FOR SEQ ID NO: 140:

(i) SEQUENCE CHARACTERISTICS:
             (A) LENGTH: 20
             (B) TYPE: nucleic acid
             (C) STRANDEDNESS: double
             (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:140:

GGATGCATCT CTGGTCATTG                                                        20

(2) INFORMATION FOR SEQ ID NO: 141:

(i) SEQUENCE CHARACTERISTICS:
             (A) LENGTH: 18
             (B) TYPE: nucleic acid
             (C) STRANDEDNESS: double
             (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:141:

CTGGATGGTA TGGTGAGG                                                          18

(2) INFORMATION FOR SEQ ID NO: 142:

(i) SEQUENCE CHARACTERISTICS:
             (A) LENGTH: 20
             (B) TYPE: nucleic acid
             (C) STRANDEDNESS: double
             (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:142:

GGAGGCCAAC AATTATTTCC                                                        20

(2) INFORMATION FOR SEQ ID NO: 143:

(i) SEQUENCE CHARACTERISTICS:
             (A) LENGTH: 20
             (B) TYPE: nucleic acid
             (C) STRANDEDNESS: double
             (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:143:

TAACAAACCG ATAATGGCGC                                                      20

(2) INFORMATION FOR SEQ ID NO: 144:

(i) SEQUENCE CHARACTERISTICS:
            (A) LENGTH: 20
            (B) TYPE: nucleic acid
            (C) STRANDEDNESS: double
            (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:144:

CATCTTGTTA GAGGGATTGG                                                      20

(2) INFORMATION FOR SEQ ID NO: 145:

(i) SEQUENCE CHARACTERISTICS:
            (A) LENGTH: 22
            (B) TYPE: nucleic acid
            (C) STRANDEDNESS: double
            (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:145:

CTCTTGAAAC TGGGAGACTT GA                                                   22

(2) INFORMATION FOR SEQ ID NO: 146:

(i) SEQUENCE CHARACTERISTICS:
            (A) LENGTH: 20
            (B) TYPE: nucleic acid
            (C) STRANDEDNESS: double
            (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:146:

CCGTCAATTC MTTTRAGTTT                                                      20

(2) INFORMATION FOR SEQ ID NO: 147:

(i) SEQUENCE CHARACTERISTICS:
            (A) LENGTH: 21
            (B) TYPE: nucleic acid
            (C) STRANDEDNESS: double
            (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:147:

GGTGGAGCTT CAATTGGAGA G                                                 21

(2) INFORMATION FOR SEQ ID NO: 148:

(i) SEQUENCE CHARACTERISTICS:
            (A) LENGTH: 25
            (B) TYPE: nucleic acid
            (C) STRANDEDNESS: double
            (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:148:

GTGTAACCTA CTTTCATAAC ACCAG                                             25

(2) INFORMATION FOR SEQ ID NO: 149:

(i) SEQUENCE CHARACTERISTICS:
            (A) LENGTH: 20
            (B) TYPE: nucleic acid
            (C) STRANDEDNESS: double
            (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO: 149:

TTGGAAACGG TTAAAACGAA                                                   20

(2) INFORMATION FOR SEQ ID NO: 150:

(i) SEQUENCE CHARACTERISTICS:
            (A) LENGTH: 20
            (B) TYPE: nucleic acid
            (C) STRANDEDNESS: double
            (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:150:

GAACCTTCCC ATCAAAAACA                                                20

(2) INFORMATION FOR SEQ ID NO: 151:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:151:

TCGCATCAAA CTGACAAACG                                                20

(2) INFORMATION FOR SEQ ID NO: 152:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:152:

GCAGGTACTC TATAAGTGCC                                                20

(2) INFORMATION FOR SEQ ID NO: 153:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:153:

GACATAAAAG CTAGGAATTT                                                20

(2) INFORMATION FOR SEQ ID NO: 154:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:154:

AAATCGGATT AACATTATCC                                                          20

(2) INFORMATION FOR SEQ ID NO: 155:

(i) SEQUENCE CHARACTERISTICS:
                  (A) LENGTH: 20
                  (B) TYPE: nucleic acid
                  (C) STRANDEDNESS: double
                  (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:155:

CTAGTTTGGT AATATCTCCT                                                          20

(2) INFORMATION FOR SEQ ID NO: 156:

(i) SEQUENCE CHARACTERISTICS:
                  (A) LENGTH: 20
                  (B) TYPE: nucleic acid
                  (C) STRANDEDNESS: double
                  (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:156:

TAATGCTATA TCTTATAGGG                                                          20

(2) INFORMATION FOR SEQ ID NO: 157:

(i) SEQUENCE CHARACTERISTICS:
                  (A) LENGTH: 20
                  (B) TYPE: nucleic acid
                  (C) STRANDEDNESS: double
                  (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:157:

TAGATAAAGT TAAAACAAGC                                                          20

(2) INFORMATION FOR SEQ ID NO: 158:

(i) SEQUENCE CHARACTERISTICS:
                  (A) LENGTH: 20
                  (B) TYPE: nucleic acid
                  (C) STRANDEDNESS: double
                  (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:158:

TAACTTACCG TGGACCCTTC                                                    20

(2) INFORMATION FOR SEQ ID NO: 159:

(i) SEQUENCE CHARACTERISTICS:
             (A) LENGTH: 20
             (B) TYPE: nucleic acid
             (C) STRANDEDNESS: double
             (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:159:

ATGGCAGCAT CAGCTTGATA                                                    20

(2) INFORMATION FOR SEQ ID NO: 160:

(i) SEQUENCE CHARACTERISTICS:
             (A) LENGTH: 20
             (B) TYPE: nucleic acid
             (C) STRANDEDNESS: double
             (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:160:

TTTCCAATAA CCACCCGTTT                                                    20

(2) INFORMATION FOR SEQ ID NO: 161:

(i) SEQUENCE CHARACTERISTICS:
             (A) LENGTH: 20
             (B) TYPE: nucleic acid
             (C) STRANDEDNESS: double
             (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:161:

CTAGTGCATT TGTTATTCAA                                                    20

(2) INFORMATION FOR SEQ ID NO: 162:

(i) SEQUENCE CHARACTERISTICS:

```
        (A) LENGTH: 20
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:162:

TGCATTGACA CCATAGTACT                                              20

(2) INFORMATION FOR SEQ ID NO: 163:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:163:

ACGGCTATAT ACATTCAATT                                              20

(2) INFORMATION FOR SEQ ID NO: 164:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:164:

TCCATCGATA ATATACCTAA                                              20

(2) INFORMATION FOR SEQ ID NO: 165:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:165:

AACTGGAGGA AGGTGGGGAT                                              20
```

(2) INFORMATION FOR SEQ ID NO: 166:

(i) SEQUENCE CHARACTERISTICS:
        (A) LENGTH: 19
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:166:

AGGAGGTGAT CCAACCGCA        19

(2) INFORMATION FOR SEQ ID NO: 167:

(i) SEQUENCE CHARACTERISTICS:
        (A) LENGTH: 15
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:167:

CCACCTTGAC TATTT        15

(2) INFORMATION FOR SEQ ID NO: 168:

(i) SEQUENCE CHARACTERISTICS:
        (A) LENGTH: 15
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:168:

TTAATTAGGA GGTAA        15

(2) INFORMATION FOR SEQ ID NO: 169:

(i) SEQUENCE CHARACTERISTICS:
        (A) LENGTH: 26
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:169:

CGTGGAGGCG ATCACACCGC AGACGT                                              26

(2) INFORMATION FOR SEQ ID NO: 170:

(i) SEQUENCE CHARACTERISTICS:
        (A) LENGTH: 27
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:170:

AGTGCGACGG GTGCACGTCG CGGACCT                                             27

(2) INFORMATION FOR SEQ ID NO: 171:

(i) SEQUENCE CHARACTERISTICS:
        (A) LENGTH: 35
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:171:

TTGGTTGCAC TTTAAATTTT CCCATTAGTC CTATT                                    35

(2) INFORMATION FOR SEQ ID NO: 172:

(i) SEQUENCE CHARACTERISTICS:
        (A) LENGTH: 35
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:172:

CCTACTAACT TCTGTATGTC ATTGACAGTC CAGCT                                    35

(2) INFORMATION FOR SEQ ID NO: 173:

(i) SEQUENCE CHARACTERISTICS:
        (A) LENGTH: 23
        (B) TYPE: nucleic acid
        (C) STRANDEDNESS: double
        (D) TOPOLOGY: linear (ii) MOLECULE TYPE: other nucleic acid

```
        (iii) HYPOTHETICAL: no (iv) ANTI-SENSE: yes (v) FRAGMENT TYPE: internal (xi) SEQUENCE DESCRIPTION: SEQ ID NO:173:

GARATNGGNN NNGGNAARGG NCA                                                  23

(2) INFORMATION FOR SEQ ID NO: 174:

(i) SEQUENCE CHARACTERISTICS:
              (A) LENGTH: 17
              (B) TYPE: nucleic acid
              (C) STRANDEDNESS: double
              (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:174:

AAYTGRTTYT TNGTRAA                                                         17

(2) INFORMATION FOR SEQ ID NO: 175:

(i) SEQUENCE CHARACTERISTICS:
              (A) LENGTH: 22
              (B) TYPE: nucleic acid
              (C) STRANDEDNESS: double
              (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:175:

AAAATCGATG GTAAAGGTTG GC                                                   22

(2) INFORMATION FOR SEQ ID NO: 176:

(i) SEQUENCE CHARACTERISTICS:
              (A) LENGTH: 22
              (B) TYPE: nucleic acid
              (C) STRANDEDNESS: double
              (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:176:

AGTTCTGCAG TACCGGATTT GC                                                   22

(2) INFORMATION FOR SEQ ID NO: 177:

(i) SEQUENCE CHARACTERISTICS:
              (A) LENGTH: 17
```

(B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:177:

AGTTATCTAC ACGACGG                                                17

(2) INFORMATION FOR SEQ ID NO: 178:

(i) SEQUENCE CHARACTERISTICS:
        (A) LENGTH: 17
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:178:

GGCGTACTAT TCACTCT                                                17

(2) INFORMATION FOR SEQ ID NO: 179:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:179:

ACCTACTCCC AACATCAGCC                                             20

(2) INFORMATION FOR SEQ ID NO: 180:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:180:

ATATAGATCT CACTACGCGC                                             20

(2) INFORMATION FOR SEQ ID NO: 181:

(i) SEQUENCE CHARACTERISTICS:
        (A) LENGTH: 17
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:181:

AGAGAATTAT GCAGTGC                                      17

(2) INFORMATION FOR SEQ ID NO: 182:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:182:

GACAGTTACC AATGCTTAAT CA                            22

(2) INFORMATION FOR SEQ ID NO: 183:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:183:

CAGCTACATC GACTATGCGA                                20

(2) INFORMATION FOR SEQ ID NO: 184:

(i) SEQUENCE CHARACTERISTICS:
        (A) LENGTH: 19
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:184:

GGGCTTCGGT GTACCTCAT                                         19

(2) INFORMATION FOR SEQ ID NO: 185:

(i) SEQUENCE CHARACTERISTICS:
      (A) LENGTH: 20
      (B) TYPE: nucleic acid
      (C) STRANDEDNESS: double
      (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:185:

AGCTCGTATG GCACCGGAAC                                        20

(2) INFORMATION FOR SEQ ID NO: 186:

(i) SEQUENCE CHARACTERISTICS:
      (A) LENGTH: 20
      (B) TYPE: nucleic acid
      (C) STRANDEDNESS: double
      (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:186:

TTGACCTCCC ACCCGACTTG                                        20

(2) INFORMATION FOR SEQ ID NO: 187:

(i) SEQUENCE CHARACTERISTICS:
      (A) LENGTH: 23
      (B) TYPE: nucleic acid
      (C) STRANDEDNESS: double
      (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:187:

CATCGCCGTC CCCGAATTTC AAA                                    23

(2) INFORMATION FOR SEQ ID NO: 188:

(i) SEQUENCE CHARACTERISTICS:
      (A) LENGTH: 21
      (B) TYPE: nucleic acid
      (C) STRANDEDNESS: double
      (D) TOPOLOGY: linear (ii) MOLECULE TYPE: other nucleic acid -continued

```
    (iii) HYPOTHETICAL: no (iv) ANTI-SENSE: no (v) FRAGMENT TYPE: internal (xi) SEQUENCE DESCRIPTION: SEQ ID NO:188:

GATGCGGAAG ATACCGTGGC T                                                     21

(2) INFORMATION FOR SEQ ID NO: 189:

(i) SEQUENCE CHARACTERISTICS:
          (A) LENGTH: 24
          (B) TYPE: nucleic acid
          (C) STRANDEDNESS: double
          (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:189:

TTAATAGCAC CCGGTACAAG CAGG                                                  24
```

METHOD COMPOSITIONS AND KIT FOR DETECTION

This application is a continuation-in-part of U.S. patent applications Nos. 09/009,483 filed Jan. 20, 1998, 08/640,672 filed May 1, 1996, now U.S. Pat. No. 5,789,168, 08/684,498 filed Jul. 19, 1996, now U.S. Pat. No. 5,830,657, and 08/807,138 filed Feb. 27, 1997, now U.S. Pat. No. 5,888,736, and of International Patent Application No. PCT/US97/07134 filed Apr. 29, 1997 designating the United States, and published as International Publication No. WO 97/41259 on Nov. 6, 1997, all of which are incorporated herein by reference.

BACKGROUND OF THE INVENTION

This application relates to a method for detection and identification of microorganisms, including in particular pathogenic microorganisms, and to compositions and kits useful in practicing the method. The invention can be applied to detection of viruses, including HIV and hepatitis, bacteria, including Chlamydia, fungi, including *Cryptococcus neoformans* and protozoa, including *Trypanosoma cruzi*. This application also relates to DNA sequencing reactions, and in particular to improved bi-directional sequencing reaction protocols making use of thermally stable polymerase enzymes.

Detection of the presence of pathogenic microorganisms through DNA-based technology is emerging as an important tool in the diagnosis of many diseases. For example, diagnosis of *Chlamydia trachomatis* infections, the most common bacterial sexually transmitted disease in North America, is shifting from traditional methods such as culture, enzyme immunoassay (EIA) and direct fluorescent antibodies (DFA) to DNA-hybridization diagnostics. Roche Diagnostic Systems, Inc. (Nutley, N.J.) manufactures Amplicor™, a test which detects *C. trachomatis* and *Neisseria gonorrohoeae* by the hybridization of a pathogen specific probe to PCR amplified products, detectable by a color change/optical density technique. Abbott Laboratories (Abbott Park, Ill.) makes UriProbe, also a test for *C. trachomatis* and *N. gonorrohoeae*, which relies on the ligase chain reaction (LCR). The LCR method, described in Patent Applications WO 9320227, WO 9300447, WO 9408047, WO 9403636, EP 477 972 uses thermostable ligase enzyme to ligate two DNA probes which hybridize in ligatable juxtaposition on a template DNA strand, thus generating a detectable ligated DNA fragment only if the template DNA is present. A multiplex PCR assay for *C. trachomatis* has also been described in Mahony et al., *J. Clin. Microbiol.* 33: 3049–3053 (1995).

The ideal DNA sequencing procedure for use in a diagnostic environment would have the following characteristics: (1) it would be able to utilize a DNA-containing sample which had been subjected to only minimal pretreatment to make the DNA accessible for sequencing; (2) it would require combining this sample with only a single reaction mixture, thus reducing risk of error and contamination, and increasing the ease with which the procedure can be automated; and (3) it would require a short amount of time to perform the sequence determination, thus decreasing the marginal costs in terms of equipment and labor for performing the test.

A wide variety if infectious pathogens that can be detected by DNA-based methods are listed in *Diagnostic Molecular Microbiology*, Persing et al., eds. American Society for Microbiology, Washington D.C. (1993). This text details diagnostic tests for bacteria, virus, fungi, and protozoa. Diagnostic tests are also proposed for identifying the presence of drug resistance genes or toxin genes.

Although these tests are generally effective for identifying an infectious disease-causing organism if present, they do not routinely provide information concerning the specific serotype, variant or form of the infecting organism. Depending on the organism in question, this information can be significant in determining the likely course of the infection, for determining the most appropriate therapeutic approach and for epidemiological purposes. Furthermore, the previously known assays involve several steps and are therefore more susceptible to systematic error than would be a test with fewer steps. Thus, there remains a need for a simple test format which is generally applicable to the detection of microorganisms, including infectious disease-causing microorganisms, and particularly for a simple test which provides an indication of the specific nature, e.g., the serotype, of the organism. It is an object of the present invention to provide such a test.

It is an object of the present invention to provide reagent combinations useful in performing tests for infectious disease-causing microorganisms, including Chlamydia human papilloma virus(HPV) and HIV.

It is a further object of the present invention to provide kits useful in performing tests for infectious disease-causing microorganisms, including Chlamydia, HPV and HIV.

It is an additional object of the present invention to provide an improved method for bi-directional sequencing of DNA samples which is well-suited for use in the diagnostic environment and for automation.

It is an additional object of the invention to provide a method for bi-directional sequencing of DNA which utilizes a DNA-containing sample which has been subjected to only minimal pretreatment to make the DNA accessible for sequencing.

It is still a further object of the invention to provide a method for bi-directional sequencing of DNA which requires combining a complex DNA-containing sample with only a single reaction mixture, thus reducing risk of error and contamination, and increasing the ease with which the procedure can be automated.

SUMMARY OF THE INVENTION

The present invention provides a method for the evaluation of a sample for the presence of a target microorganism which can be performed directly on a natural abundance DNA preparation obtained from the sample in a single reaction vessel. The method of the invention comprises the steps of:

(a) combining the natural abundance DNA preparation with first and second primers, a nucleotide triphosphate feedstock mixture, a chain-terminating nucleotide triphosphate and a thermally stable polymerase enzyme which incorporates dideoxynucleotides into an extending nucleic acid polymer at a rate which is no less than 0.4 times the rate of incorporation of deoxynucleotides to form a reaction mixture, said first and second primers binding to the sense and antisense strands of the DNA of the target microorganism, respectively, and flanking a selected region within the genome of the target microorganism;

(b) exposing the reaction mixture to a plurality of temperature cycles each of which includes at least a high temperature denaturation phase and a lower temperature extension phase, thereby producing a plurality of species of terminated fragments if DNA from the target microorganism is present in the sample, each species of terminated fragment corresponding to a different incorporation position for the chain-terminating nucleotide triphosphate in the DNA of the target microorganism; and (c) evaluating the terminated fragments produced to determine the incorporation positions of the chain-terminating nucleotide triphosphate. Based on the incorporation positions, not only the presence but also the specific nature, e.g. the serotype, of any target microorganism present can be determined.

The present invention also provides a composition comprising a mixture of four deoxynucleotide triphosphates and at least one dideoxynucleotide triphosphate corresponding to one of the four deoxynucleotide triphosphates, wherein the dideoxynucleotide triphosphate is present in a mole ratio to the corresponding deoxynucleotide triphosphate of from 1:50 to 1:500, said composition further comprising a thermally stable polymerase enzyme which incorporates dideoxynucleotides into an extending nucleic acid polymer at a rate which is no less than 0.4 times the rate of incorporation of deoxynucleotides.

Also provided is a kit for detection of a target microorganism comprising, in packaged combination, the above composition and a pair of primers which bind to the sense and antisense strands, respectively, and flank a selected region within the genome target microorganism.

The present invention also provides a method for bi-directional sequencing a region of interest in a DNA sample. The method can be carried out using a single set of reagents which is added to a minimally-treated sample to produce useful sequencing results.

DETAILED DESCRIPTION OF THE INVENTION

The compositions and kits of the present invention can be employed in a bi-directional DNA sequencing method in many contexts including: (1) detection of mutations, particularly mutations of medical significance, in samples derived from a human patient, animal, plant or microorganism; (2) determination of HLA type ancillary to transplant procedures; (3) detection and identification of microorganisms, particularly pathogenic microorganisms, in a sample; and (4) in-situ sequencing reactions to produce sequencing fragments within a histological specimen which are then removed from a selected location on the tissue preparation and loaded onto a gel for sequence analysis. This latter approach is particularly useful for evaluation of archived samples in retrospective studies where the outcome of a disease condition is known, but the potentially causative mutation is not. This method can be used with labeled primers for single base sequencing (or multiple-base sequencing using multiple tissue samples).

In the context of detecting and identifying microorganisms, the invention provides a novel approach to the evaluation of a sample for the presence of a target microorganism and for the identification of the specific nature of any organism found to be present. The target microorganism may be virus, bacteria, fungi or protozoa. Specific non-limiting examples of microorganisms to which the invention can be suitably applied include bacteria such as *Mycobacteria tuberculosis, Rickettsia rickettsii, Ehrlichia chaffeensis, Borrelia burgdorferi, Yersinia pestis, Treponema pallidum, Chlamydia trachomatis, Chiamydia pneumoniae, Mycoplasma pneumoniae*, Mycoplasma sp., *Legionella pneumophila, Legionella dumoffii, Mycoplasma fermentans*, Ehrlichia sp., *Haemophilus influenzae, Neisseria meningitidis, Streptococcus pneumonia, S. agalactiae*, and *Listeria monocytogenes*; viruses such as Human Immunodeficiency Virus Type 1 (HIV-1), Human T-Cell Lymphotrophic Virus Type 1 (HTLV-1), Hepatitis B Virus (HBV), Hepatitis C Virus (HCV),Herpes Simplex, Herpesvirus 6, Herpesvirus 7, Epstein-Barr Virus, Cytomegalovirus, Varicella-Zoster Virus, JC Virus, Parvovirus B19, Influenza A, B and C, Rotavirus, Human Adenovirus, Rubella Virus, Human Enteroviruses, Genital Human Papillomavirus (HPV), and Hantavirus; fungi such as *Cryptococcus neoformans, Pneumocystis carinii, Histoplasma capsulatum, Blastomyces dermatitidis, Coccidioides immitis*, and *Trichophyton rubrum*; and protozoa such as *Trypanosoma cruzi*, Leishmania sp., *Plasmodium, Entamoeba histolytica, Babesia microti, Giardia lamblia*, Cyclospora sp. and Eimeria sp. The method of the invention may also be used for Cryptosporidium oocyst detection; for identification of bacterial toxin genes, such as the toxin genes from *Vibrio cholerae* 01, enterotoxigenic *Escherichia coli*, Shigella sp., enteroinvasive *E. coli, Helicobacter pylori* (formerly *Campylobacter pylori*), toxigenic *Clostridium difficile, Staphylococcus aureus*, and *Streptococcus pyogenes* exotoxins; and for identification of anti-microbial resistance loci such as rifampin resistance mutations in *Mycobacterium tuberculosis* and *M. leprae*; HIV Drug Resistance, erm Erythromycin Resistance Genes, methicillin—resistance genes in Staphylococcus, Penicillinase-Producing genes in *Neisseria gonorrhoeae*, genes encoding aminoglycoside-modifying enzymes, genes encoding an extended spectrum of Beta-Lactamases, fluoroquinolone and isoniazid resistance mutations in *Mycobacterium tuberculosis*, and genes encoding vancomycin resistance in Enterococci.

The method of detecting and identifying the presence of a target microorganism may utilize bi-directional DNA sequencing, in which a natural abundance DNA-containing sample suspected to contain the target microorganism is combined in a reaction mixture with (1) first and second primers that hybridize with the sense and antisense strands of the DNA of the target microorganism, respectively, and flank a selected region within the genome of the target microorganism, (2) a nucleotide triphosphate feedstock mixture, (3) at least one chain-terminating nucleotide triphosphate and (4) a polymerase enzyme which incorporates dideoxynucleotides into an extending nucleic acid polymer at a rate which is no less than 0.4 times the rate of incorporation of deoxynucleotides to form a reaction mixture. This reaction mixture is processed through a plurality of thermal cycles. Each thermal cycle includes at least an extension step which is performed at a temperature of around 68 to 75° C. and a denaturation step performed at a temperature of around 90 to 98° C. In addition, the thermal cycles may include a separate annealing step performed at a temperature of 50 to 70° C.

During each cycle, the primers each anneal to the respective strand of any target DNA present in the sample, and primer chain extension using the polymerase enzymes and the nucleotide triphosphate feedstocks proceeds until terminated by incorporation of a chain-terminating nucleotide triphosphate. This results in the production of sequencing fragments comparable to those generated in a conventional sequencing reaction. Analysis of these fragments provides information concerning the sequence of the selected region of the target DNA, and thus of the serotype of the target microorganism. Those extension products which are not terminated prior to reaching the region complementary to the other primer can serve as template for generation of sequencing fragments in later cycles, although this generally occurs to a very small extent. This method also provides for simultaneously determining the positions of a selected nucleotide base in a target region of both strands of a denatured duplex nucleic acid polymer. The method of the invention differs from the prior art, because the first and second oligonucleotide primers are each labeled with different, spectroscopically-distinguishable fluorescent labels. The method therefore obtains information about both DNA strands simultaneously while providing improved sensitivity as a result of the non-linear increase in the amount of DNA which results from the production of additional templates molecules from unterminated fragments.

Among the advantages of the present invention is the ability to perform an evaluation directly on a "natural abundance" DNA sample. The nature of the initial sample will depend on the nature of the target microorganism. For example, in the case of Chlamydia, the initial sample employed in the present invention is suitably a urine sample, genital scraping or genital swab taken from a human patient, although other samples which are suspected of containing Chiamydia can also be tested using the method of the invention. Similarly, to test for HIV infection, the preferred sample is a blood sample.

As used herein a "natural abundance sample" is a sample which has been treated to make DNA in the sample accessible for hybridization with oligonucleotide primers, for example by lysis, centrifugation to remove cellular debris and proteolytic digestion to expose the DNA, but which has not been subjected to a preferential purification or amplification step to increase the amount of target DNA relative to non-target DNA present in the initial sample. The term "natural abundance" does not, however, require the presence of all the DNA from the original sample. Thus, a complex sample containing just nuclear DNA, or just mitochondrial DNA or some subfraction of nuclear or mitochondrial DNA obtained by isolation from a tissue sample but not subjected to preferential amplification would be a "natural abundance" sample within the meaning of that term in the specification and claims of this application. The term "natural abundance" would also include a DNA sample prepared by conversion, for example by reverse transcription, of a total mRNA preparation or the genome of an RNA virus to cDNA; DNA isolated from an individual bacterial colony growing on a plate or from an enriched bacterial culture; and a viral DNA preparation where substantially the entire viral genome is isolated. The term "natural abundance" does not encompass a sample in which the isolated DNA is not a complex combination of DNA molecules, and thus would not encompass, for example, a purified plasmid preparation containing only a single species of plasmid.

Natural abundance samples of mammalian DNA can be prepared from fluid samples, e.g., blood or urine or tissue samples by any of a number of techniques, including lysis, centrifugation to remove cellular debris and proteolytic digestion to expose the DNA; salt precipitation or standard SDS-proteinase K-phenol extraction. Natural abundance samples can also be prepared using kits, for example the Gentra PURE GENE DNA Isolation Kit.

Primers used in the method of the present invention can be any pair of primers which hybridize with the sense and antisense strands DNA of the target microorganism flanking a selected region of diagnostic relevance, and which do not both hybridize to neighboring locations in human DNA or other microbial DNA potentially found in the sample. As used herein, the term "flanking" will be understood to mean the positioning of primers at the 5'-ends of the selected region on each DNA strand, such that extension of the primers leads to replication of the region between the primers. The primers are preferably selected such that the primer pair flanks a region that is about 500 bp or less, although primers spanning larger regions of DNA can be utilized with adjustments to the sequencing mixture (generally an increase in the relative amount of deoxynucleotide triphosphates) to increase the amount of longer sequencing fragments produced.

Primers can be selected to hybridize with highly conserved regions which are the same in all variants of the target microorganism or can be prepared as degenerate primers to take known sequence variations at the primer site into account. Thus, the first and second primers of the invention may each be a discrete oligonucleotide species, or may be a set of oligonucleotide primers with similar but not identical sequences. Primers can also be selected to bind to the sense and antisense strands of DNA flanking a region of the genome of the target microorganism which is constant across all known variants and forms of the microorganism, in which case the method of the invention would provide detection but not any specific qualitative characterization of the microorganisms, i.e,. such primers could not provide discrimination between subspecies, serovars, strains, subtypes, biovars, variants, serotypes or between closely related species of the target microorganism. An example of such a primer pair is a primer pair that binds to the cryptic plasmid of C. trachomatis which is recognized as a suitably specific target sequence or detection purposes, but which is not known to vary from strain to strain. Preferably, however, the primers employed will flank a region of the target genome which is variable in sequence depending on the serotype of the organism. Thus, for C. trachomatis primers which flank portions of the omp1 gene are preferred. Similarly, in the case of HIV detection, primers flanking known mutation sites in the HIV protease gene or reverse transcriptase gene produce fragments which permit both detection of HIV and the identification of the HIV variant present in the sample. Primers MY09 and MY11 (See example 10) give sequence information for most relevant types of human papilloma virus (HPV) but not other viruses.

In an alternative embodiment, primer pairs are selected which, when treated under the conditions of the invention, give sequence information from a much wider variety of organisms. This is the case with eubacterial "universal" primers such as 91E and 13B listed in Appendix I which can be used to obtain sequence data from the 16S rDNA gene of many bacteria. These primers are useful for identifying which bacterium is present in a septic blood culture, or any other pure but unknown culture. Patient samples which contain a broad range of bacteria will give a complex result, consisting of many overlapping sequences when tested with these primers. The complex result may, in some cases, provide useful information about the bacteria present. However, in the normal course, it is advantageous to separate out the species, i.e. by plating them out first. In this case, individual pure colonies can be selected and identified.

In still another embodiment, the primer pairs are selected to determine whether a specific gene is present in the patient sample. The gene can be a toxin gene, a virulence gene, an anti-biotic resistance gene or a specific mutation which confers drug resistance or the like. Such a test can determine if a micro-organism is present and if it carries the gene at the same time.

Primers for other microorganisms can be derived from known sequence information. Appendix I lists a collection of suitable primer pairs for various other microorganisms which are taken from Persing et al., supra.

One or both of the primers may be labeled with a detectable label at the 5'-end thereof, particularly a fluorescent label such as fluorescein or a cyanine dye such as Cy 5.5. If labels are used on both primers, the labels selected should be spectroscopically-distinct, i.e., they should have either a different excitation spectrum or a different emission spectrum such that one primer can be distinguished from the other. When both primers are labeled with different detectable labels, the sequence of both strands of the sample can be determined in a single reaction.

The nucleotide triphosphate feedstock mixture is a standard mixture of the four conventional bases (A, C, G and T) in a buffer suitable for template-dependent primer extension with the enzyme employed. As will be appreciated by persons skilled in the art, the specific concentrations of the nucleotide triphosphates and the nature of the buffer will vary depending on the enzyme employed. Standard buffers and reagent concentrations for various known polymerase enzymes may be employed in the invention.

The reaction mixture used in the present invention also includes at least one type of chain-terminating nucleotide triphosphate. Separate reactions for the four different types of bases may be run either concurrently or successively. Running all four bases concurrently comports with conventional sequencing practice. However, a preferred embodiment of the present invention combines the single vessel methodology of this application with "single track sequencing" which is described in commonly assigned U.S. Pat. No. 5,835,189. In single track sequencing, the determination of the positions of only one (or in any event less than 4) nucleotide(s) of a target sequence is frequently sufficient to establish the presence of and determine the qualitative nature of a target microorganism by providing a finger-print or bar-code of the target sequence that may be sufficient to distinguish it from all other known varieties of the sequence. Throughput is increased by reducing the number of reactions and electrophoresis runs required to identify a sequence. By selection of the order of bases tested, and intermediate analysis, it may be unnecessary to run all four bases to determine the presence and specific qualitative nature of any target microorganism present in the sample.

The polymerase enzyme used in the invention is a thermostable polymerase enzyme which incorporates dideoxynucleotides into an extending nucleic acid polymer at a rate which is no less than 0.4 times the rate of incorporation of deoxynucleotides. ThermoSequenase™ is exemplary of such an enzyme. Reeve et al., Nature 376: 796–797 (1995). Tabor et al. have also described enzymes which have increased processivity and increased levels of incorporation of dideoxynucleotides. (See EP-A1-0 655 506, which is incorporated herein by reference) Roche sells an enzyme under the trademark TAQ-FS which meets these criteria as well.

The absolute and relative amounts of nucleotide triphosphates and chain-terminating nucleotide triphosphates may be optimized for the particular enzyme employed. In general, however, the nucleotide triphosphates will be included at in the reaction mixture at concentrations of from 250 $\mu$M to 1.5 mM, and the chain-terminating nucleotide triphosphate will be included at a level of from 0.5 $\mu$M to 30 $\mu$M to produce compositions in which the mole ratio of the chain terminating nucleotide triphosphate to the corresponding nucleotide triphosphate is from 1:50 to 1:1000, preferably from 1:100 to 1:500. This will result in incorporation of a chain-terminating nucleotide triphosphate into from 30 to 100 percent of the extending polymer chains formed during the thermal cycling of the reaction mixture.

The method of the invention is suitably practiced using a kit which provides the appropriate reagents in conveniently packaged form. To reduce the number of sample preparation steps, and thus to reduce the risk of erroneous results, such a kit will suitably include at least one pre-prepared mixture comprising all four nucleotide triphosphates and at least one chain terminating nucleotide triphosphate, where the mole ratio of chain terminating nucleotide to the corresponding deoxynucleotide triphosphate is from 1:50 to 1:1000, preferably 1:100 to 1:500.

The invention will now be further described by way of the following non-limiting examples.

EXAMPLE 1

The presence of the sexually transmitted disease pathogen *Chlamydia trachomatis* in a patient sample is detected according to the method of the invention as follows.

Urine samples from patients suspected of carrying a sexually transmitted disease pathogen are prepared for sequence-based diagnosis as follows. 100 ul of first void urine are deposited in a sterile microcentrifuge tube. The tube is centrifuged at 12,000×g for 20 min; the supernatant is removed. 100 ul of Lysis Solution (Proteinase K @ 100 g/ml; 1% Tween 20) is added to the bacterial pellet and incubated 1 h at 55° C., or 18 h at room temperature. After a final incubation at 95° C. for 10 minutes, 200 ul of Geneclean II glass milk is added, according to the manufacturer's instructions. (Bio 101, Inc) DNA is eluted in 10 ul of double distilled $H_2O$. (A lysis solution control may be prepared if desired, by adding the lysis solution to a sterile tube (a tube without any urine pellet), and treating this tube like the others.)

The sample natural abundance DNA is then treated according to the method of the invention with a pair of primers and reagents to identify the sequence of a *C. trachomatis* gene present in the sample, if any. A suitable *C. trachomatis* specific target for sequencing is the cryptic plasmid. Primers that may be used are

| Name | Sequence | |
|---|---|---|
| KL1: | TCCGGAGCGA GTTACGAAGA | [SEQ ID NO: 1] |
| KL2: | ATTCAATGCC CGGGATTGGT | [SEQ ID NO: 2] |

These sequencing primers were employed previously for PCR amplification reactions, but not sequencing (Mahony et al., "Confirmatory polymerase chain reaction testing for *Chlamydia trachomatis* in first void urine from asymptomatic and symptomatic men" *J. Clin Microbiol.* 30:2241–2245 (1992)).

Either primer may be labeled at the 5'-end with a detectable label such as a Cy5.5 fluorophore. If both primers are labeled, they should be distinguishable. Labels are selected on the basis of the instrument employed for detection. Labeling reactions are performed according to methods well known in the art, such as amidite labeling or dye-ester condensation.

The sequencing reaction mixture is prepared by combining 2.5 ul of the prepared DNA sample, 0.67 ul of 10 uM primer KL1 (labeled with Cy5.5), 0.45 ul of KL2 primer at 10 uM, 2 ul of THERMOSEQUENASE reaction buffer (250 mM Tris-HCl pH 9.0 @ 25° C., 39 mM MgCl$_2$), 2 ul of THERMOSEQUENASE enzyme (Amersham Life Sciences) diluted 1/10 in the dilution buffer provided with the enzyme and 5.38 ul of double distilled H$_2$O. The final volume is 13 ul.

3 ul of the sequencing reaction mixture is placed in each of 4 clean tubes and covered with one drop of mineral oil (Sigma Chemical Co., Cat #M-5904). The tube is placed in a PTC-100 thermal cycler (M. J. Research, Maine) and heated for 3 min at 94° C., then cooled to 85° C. One of the following termination mixtures are then added to each of the 4 tubes:

3 ul of dNTP:ddATP (1 mM each dNTP, 3.3 uM ddATP) in tube A.

3 ul of dNTP:ddCTP (1 mM each dNTP, 3.3 uM ddCTP) in tube C.

3 ul of dNTP:ddGTP (1 mM each dNTP, 3.3 uM ddGTP) in tube G.

3 ul of dNTP:ddTTP (1 mM each dNTP, 3.3 uM ddTTP) in tube T.

The dNTP:ddNTP mixes are preferably heated to 85° C. when added to the tube. The reaction mixture is mixed well and it is subjected to the following thermal cycling regime for 55 cycles:

94° C./30 sec.

60° C./30 sec.

70° C./1 min.

After the last cycle, the tubes are kept at 70° C. for 2 min, then cooled to 4° C. until ready for loading. To view the reaction products, 6 ul of loading buffer (dye/stop solution) is added to each tube. The aqueous phase (the bottom phase disposed under the oil layer) is removed and put it in another tube. The sample is heated to 75° C. for 3 min, and put on ice. 2 ul of each sample is loaded in each well of a MicroGene Blaster automated DNA sequencer (Visible Genetics Inc., Toronto, ON). The reaction products are electrophoretically separated and detected. The data is analyzed using GeneObjects software (Visible Genetics Inc., Toronto, ON) to base-call (i.e. determine the DNA sequence) of the samples. The base-called sequence is compared to the known *C. trachomatis* sequence to confirm diagnosis. Results are reported to the patient file.

EXAMPLE 2

The method of the invention may be employed to identify not only the presence of *C. trachomatis* in a patient sample but also the strain identity. Health care workers currently seek to distinguish among *Chlamydia trachomatis* strains to determine the molecular epidemiologic association of a range of diseases with infecting genotype (See Dean, D. et al "Major Outer Membrane Protein Variants of *Chlamydia trachomatis* Are Associated with Severe Upper Genital Tract Infections and Histopathology in San Francisco." J. Infect. Dis. 172:1013–22 (1995)).

A suitable strain specific target for *C. trachomatis* is the omp1 (outer membrane protein) gene which has at least 4 variable sequence ("VS") domains that may be used to distinguish among the 15 known genotypes of *C. trachomatis* (Yuan, Y et al. "Nucleotide and Deduced Amino Acid Sequences for the Four Variable Domains of the Major Outer Membrane Proteins of the 15 *Chlamydia trachomatis* Serovars" Infect. Immun. 57 1040–1049 (1989)).

Strain identification is achieved using the method of Example 1 with the following modifications. First of all, because of the length of the VS domains, separate reactions are performed to obtain sequence from VS1/VS2 and VS3/VS4. The following oligonucleotide primers may be employed:

For VS1/VS2:

| Name | Sequence | |
|------|----------|---|
| MF21 | CCGACCGCGT CTTGAAAACA GATGT | [SEQ. ID NO. 3] |
| MB22 | CACCCACATT CCCAGAGAGC T | [SEQ. ID NO. 4] |

For VS3/VS4

| Name | Sequence | |
|------|----------|---|
| MVF3 | CGTGQAGCTT TGTGGGAATG T | [SEQ. ID NO. 5] |
| MB4 | CTAGATTTCA TCTTGTTCAA TTGC | [SEQ. ID NO. 6] |

These sequencing primers were employed previously for PCR amplification reactions, but not sequencing. Mahoney et al., supra.

These oligonucleotide primers are used in separate reactions in place of KL1 and KL2 in Example 1. The sample preparation and sequencing reactions are performed as in Example 1. The reaction products are electrophoretically separated and detected on a MicroGene Blaster automated DNA sequencing apparatus (Visible Genetics Inc., Toronto, ON). The data is analyzed using GeneObjects software to base-call the samples and to compare the data to the known varieties of *C. trachomatis*. Pure populations generally give unambiguous sequence data. Where heterozygous mixed populations are detected, a circumstance thought to occur in 1–3% of clinical *C. trachomatis* samples, the software identifies the strains which could be combined to result in the particular heterozygote sample detected.

EXAMPLE 3

Strain-specific *C. trachomatis* identification over the VS1/VS2 domain can be achieved according to the method in Example 1, by using the following degenerate primers sets:

```
Forward
OMP291: AGCATGCGTR TKGGTTACTA YGG [SEQ ID NO. 7]
(labeled with Cy5.5). Base 175 to 197 of the QRF
of the omp1 gene of C. trachomatis.

Forward
OMP314A: TGACTTTGTT TTCGACCGYG TTTT [SEQ ID NO. 8]
(labeled with Cy5.5). Base 198 to 221 of the ORF
of the omp1 gene of C. trachomatis.

Reverse
OMP722: CTAAAGTYGC RCATCCACAT TCC [SEQ ID NO. 9]
Base 637 to 615 of the ORF of the omp1 (in serovar
K) gene of C. trachomatis. The primer may not have
the EXACT SAME sequence as in serovar K.

Reverse
OMP711: CATCCACATT CCCASARAGC TGC [SEQ ID NO. 10]
Base 626 to 604 of the ORF of the omp1 (in serovar
K) gene of C. trachomatis. The primer may not have
the exact same sequence as in serovar K.
```

These primers sets are preferably used in the following combinations:

(1) OMP291-OMP722, sequencing a 455 to 463-bp (depending on the serotype) fragment of the omp1 gene of *C. trachomatis*; or (2) OMP314A-OMP711, sequencing a 421 to 430-bp (depending on the serotype) fragment of the omp1 gene of C. trachomatis.

EXAMPLE 4

The method as exemplified in Examples 1, 2 and 3 may be further improved by employing different labels, preferably fluorescent labels, on the different primers for use in a multi-dye sequencer. This method takes advantage of the fact that a given termination mixture containing, for example, ddATP will give chain termination products for the A nucleotide in both directions. The different primer labels means that one reaction mixture loaded in a single lane of an automated DNA sequencing apparatus designed to detect the two labels (a "multi-dye sequencer") will identify the A nucleotide of both sense and antisense strands. Separate reactions are performed for the other 3 nucleotides. Using only 4 lanes of an electrophoresis gel, and 4 reaction mixtures, the DNA sequences of both the sense and antisense strands can be obtained. This information allows the operator to resolve any ambiguities that may be present.

Use of two different labels lends itself to a further improvement. As noted above, in a reaction according to the invention, the results of the ddATP reaction will give chain termination products for the A nucleotide in both directions. Since the A nucleotide in one direction corresponds to the T nucleotide in the other, a single reaction can provide the location of two bases. A second termination reaction with, for example, ddCTP will then obtain the positions of the other two nucleotides, C and G. Thus only two lanes of an electrophoresis gel and 2 reaction mixtures are required to identify the location of all 4 bases of the sequence.

A suitable multi-dye sequencer for use with this aspect of the invention, is the Applied Biosystems 377 Prism automated DNA sequencer (Applied Biosystems Inc., Foster City, Calif.). The fluorescent labels are selected to be detectable on the 377 instrument. Instead of the dye-terminator chemistry suggested in the Applied Biosystems product literature, however, the fluorescent labels must be conjugated to the 5' end of the primer molecules. The samples are electrophoresed, detected and the detected data is recorded.

Sophisticated software such as GeneObjects software (Visible Genetics Inc, Toronto, Calif.) may be used to assist in evaluation of the results. This software may employ the methods of commonly assigned U.S. Pat. No. 5,853,979, U.S. patent application Ser. No. 08/670,534 and International Patent Application No. PCT/US96/11130, published as WO97/02488, all of which are incorporated herein by reference. In one of the methods, the single nucleotide data tracks are evaluated and nucleotides are positioned relative to the known (or standard) DNA sequence expected from the sample. When data tracks are generated for each of the four nucleotides, the full DNA sequence of the sample may be base-called. The base-called sequence is then compared to the library of known sequences to determine which C. trachomatis strain or strains are present in the sample.

EXAMPLE 5

The sequence of both the sense strand and antisense strand of a C. trachomatis cryptic plasmid gene may be obtained in a one step reaction using the primers:

| Name | Sequence | |
|---|---|---|
| KL1: | TCCGGAGCGA GTTACGAAGA | [SEQ ID NO. 1] |
| CT1590: | ATGCCCGGGA TTGGTTGATC | [SEQ ID NO. 11] |

Combine the following materials and mix well:

| | Concentration | Amount |
|---|---|---|
| Patient Sample DNA | | 11.25 ul |
| KL1*Cy5.5 Primer | 10 uM | 3 ul |
| CT1590*Fluoresceine Primer | 10 uM | 2 ul |
| Enzyme Diluent (Amersham plc) | | 8 ul |
| ThermoSequenase Enzyme | 32 U/ul | 0.9 ul |
| double distilled H$_2$O | | 24.2 ul |

Take 11 ul of the mixture and add 2 ul of 13X buffer [Tris-HCl 260 mM pH 8.3, MgCl$_2$ 39 mM] (final concentration 20 mM Tris-HCl pH 8.3, 3 mM MgCl$_2$). Mix well and place 3 ul into each of 4 tubes. Heat tube to 94° C. for 5 mins then reduce temperature to 85° C. Add and mix 3 ul of an 85 C dNTP/ddNTP solution consisting of 0.75 mM each dNTP and 2.5 uM of a chain terminating nucleotide triphosphate (ddNTP) (use a different ddNTP in each of the 4 tubes).

Treat the mixture to 60 cycles of the following thermal cycling reactions: 94° C. for 10 sec, 62° C. for 15 sec, 70° C. for 1 min. Upon completion, treat the mixture for a final 5 min at 70 C and then store at 4° C. until ready for loading. For viewing the reaction products, add an equal volume of stop/loading solution (95% formamide plus a colored dye). Take 1.5 ul and load in a single lane of a MicroGene Blaster automated DNA sequencer (Visible Genetics Inc., Toronto). Load the remaining mixture (@ 10.5 ul) in a single lane of an ALF Automated Sequencer (Pharmacia LKB, Uppsala, Sweden). The reaction products from the Cy5.5 labeled primer are detected on the MicroGene Blaster using GeneObjects Software. The reaction products from the fluorescein labeled primer are detected on the ALF Automated Sequencer using GeneObjects Software. The base-calling results of the Cy5.5 labeled primer were compared to the known sequence of the gene by the GeneLibrarian component of GeneObjects.

EXAMPLE 6

As described in U.S. Pat. No. 5,834,189, not all 4 nucleotides of C. trachomatis, or any polymorphic or multiple allelic locus of any gene or organism necessarily need to be determined in order to ascertain which allele or variant is present. In many cases, positioning less than four nucleotides may be sufficient to determine with certainty which allele is present. The method of Examples 1–4 may be modified to obtain single nucleotide data tracks (or fragment patterns) by performing only one of the termination reactions at a time.

In the case of detection and serotyping of C. trachomatis, the evaluation of the A track alone over the first 100 nucleotides of the omp1 gene, aligning to nucleotides 249–349 of the serovars C and K, can distinguish the serovars. Appendix II is a text file representation of the omp1 gene in each of the serovars. The sequences are all aligned to the last (3') nucleotide of the detectably labeled primer omp314A. (Appendix II shows sequences starting 29 bp downstream of the 3'-nucleotide.) This illustration differs from a traditional "consensus" sequence illustrations in that all missing bases (usually represented by N's or raised dashes) are deleted. The A's are illustrated in the order and positions in which they would be expected to appear after a sequencing reaction and upon detection by an automated DNA electrophoresis apparatus.

If, in another microorganism, the A lane (or other preferred first lane) were not sufficient to distinguish all types, a second reaction for the C, G or T nucleotide could be performed to further define the qualitative nature of any target microorganism present in the sample. Because the sequences of the types are previously known, the operator can determine which of the nucleotides provide the greatest information and will analyze those nucleotides first.

EXAMPLE 7

The presence of and strain identity of *C. trachomatis* in a patient sample may be determined according to the methods of the previous examples by substituting the following primer pairs. These primers are used to determine the sequence of the omp1 gene (publicly available at DNASIS Accession No. X62921).
Forward Primer (5' Primer) labeled with a detectable label such as Cy5.5:

```
Primer    GGAGACTTTG TTTTCGACCG  [SEQ ID NO 12]
   OMP312:
Position 312-331 of X62921
``` and one of the following Reverse Primers (3' Primer) (optionally labeled with a detectable label different from the 5' primer):

```
Primer OMP708: CATTCCCACA AAGCTGCGCG [SEQ ID NO 13]
Position 727-708 of X62921

Primer OMP706: TTCCCACAAA GCTGCGCGAG [SEQ ID NO 14]
Position 725-706 of X62921

Primer OMP704: CCCACAAAGC TGCGCGAGCG [SEQ ID NO 15]
Position 723-704 of X62921
```

EXAMPLE 8

The presence of and strain identity of *C. trachomatis* in a patient sample may be determined according to the method of previous examples, using *C. trachomatis* ribosomal DNA (rDNA) specific primers such as

```
CT220  ACCTTTCGGT TGAGGGAGAG TCTA  [SEQ ID NO 16]

and

CT447  GGACCAATTC TTATTCCCAA GCGA  [SEQ ID NO 17]
```

Haydock et al., Chap 1.10 in Persing et al., supra.

EXAMPLE 9

The sequence of both the sense strand and antisense strand of the protease gene of HIV-1 integrated into natural abundance DNA of lymphocytes may be obtained in a one step reaction as follows.

Natural abundance DNA is prepared from the patient blood lymphocyte sample according to a standard method such as a standard salting-out procedure (as provided by the Puregene DNA Isolation Kit, Gentra Systems, Inc., Minneapolis) or by detergent and proteinase K treatment (Current Protocols in Molecular Biology, Eds. Ausubel, F. M. et al, (John Wiley & Sons; 1995)).

Combine the following materials and mix well:

|  | Concentration | Amount |
|---|---|---|
| Patient Sample DNA |  | 11.25 ul |
| PR211F*Cy5.5 Primer | 10 uM | 3 ul |
| or |  |  |
| PR281*Cy5.5 Primer | 10 uM | 3 ul |
| PR526*Fluorescein Primer | 10 uM | 2 ul |
| Enzyme Diluent (Amersham plc) |  | 8 ul |
| THERMOSEQUENASE Enzyme 32 U/ul |  | 0.9 ul |
| double distilled H2O |  | 24.2 ul |

The primers have the following sequences:

Name    Sequence

Choice of Forward Primers

```
PR211F  ATCACTCTTT GGCAACGACC       [SEQ ID No. 18]
(FORWARD), BASE 6 TO 25 QF THE PRQTEASE GENE
or
PR2B1   CAGGAGCAGA TGATACAGTA TTAG  [SEQ ID No. 19]
(FORWARD), BASE 76 TO 99 OF THE PROTEASE GENE
```

Reverse Primer

```
PR526:  CCATTCCTGG CTTTAATTTT ACTGG [SEQ ID No. 20]
(REVERSE), BASES 321 TO 345 OF THE PROTEASE GENE
```

PR211F-PR526 creates a sequencing fragment of maximum size 340 bp. PR281-PR526 creates a sequencing fragment of maximum size 270 bp. Both regions contain the sequence of the various codons where mutations are involved in protease inhibitor resistance (Codons 46, 48, 54, 63 82 84 and 90).

Take 11 ul of the mixture and add 2 ul of 13X buffer [Tris-HCl 260 mM pH 8.3, MgCl$_2$ 39 mM] (final concentration 20 mM Tris-HCl pH 8.3, 3 mM MgCl$_2$). Mix well and place 3 ul into each of 4 tubes. Heat tube to 94° C. for 5 mins then reduce temperature to 85° C. Add and mix 3 ul of an 85 C dNTP/ddNTP solution consisting of 0.75 mM each dNTP and 2.5 uM of a chain terminating nucleotide triphosphate (ddNTP) (use a different ddNTP in each of the 4 tubes).

Treat the mixture to 60 cycles of the following thermal cycling reactions: 94 C for 10 sec, 62 C for 15 sec, 70 C for 1 min. Upon completion, treat the mixture for a final 5 min at 70 C and then store at 4 C until ready for loading. For viewing the reaction products, add an equal volume of stop/loading solution (95% formamide plus a coloured dye). Take 1.5 ul and load in a single lane of a MicroGene Blaster automated DNA sequencer (Visible Genetics Inc., Toronto). Load the remaining mixture (@ 10.5 ul) in a single lane of an ALF Automated Sequencer (Pharmacia LKB, Uppsala, Sweden). The reaction products from the Cy5.5 labelled primer are detected on the MicroGene Blaster using GeneObjects Software. The reaction products from the fluorescein labeled primer are detected on the ALF Automated Sequencer using GeneObjects Software. The base-called results from each primer were compared to the known sequences of HIV-1 by GeneLibrarian (a component of GeneObjects (Visible Genetics Inc, Toronto).

EXAMPLE 10

The presence and type of human papilloma virus (HPV) present in a patient sample can be determined according to the method of the invention by following the protocol in Example 1 with the following modifications.

Patient sample DNA is extracted from 250 ul urine specimens using Geneclean II (Bio 101, Inc.). The sample is then treated as described previously but employing the degenerate primer pair:

```
Forward Primer: MY11
GCMCAGGGWC ATAAYAATGG      [SEQ ID No. 21]

Reverse Primer: MYO9
CGTCCMAARG GAWACTGATC      [SEQ ID No. 22]
```

The reactions are performed as before, using ThermoSequenase enzyme or the like. Reaction products are detected on an automated electrophoresis/detection device such as the MicroGene Blaster. The sequence is analyzed and compared to the known varieties of HPV to identify the type. The result is reported to the patient file.

Although the preferred embodiments of the invention has been described above in some detail, it should be appreciated that a variety of embodiments will be readily apparent to one skilled in the art. The description of the invention is not intended to be limiting to this invention, but is merely illustrative of the preferred embodiments.

We claim:

1. A composition comprising a mixture of four deoxynucleotide triphosphates and at least one dideoxynucleotide triphosphate corresponding to one of the four deoxynucleotide triphosphates, wherein the dideoxynucleotide triphosphate is present in a mole ratio to the corresponding deoxynucleotide triphosphate of from 1:50 to 1:500, said composition further comprising a thermally stable polymerase enzyme which incorporates dideoxynucleotides into an extending nucleic acid polymer at a rate which is no less than 0.4 times the rate of incorporation of deoxynucleotides.

2. The composition according to claim 1, wherein the mole ratio is from 1:100 to 1:300.

3. A kit for detection of a target microorganism comprising, in packaged combination,
   (a) a pair of primers which bind to the sense and antisense strands, respectively, and flank a selected region within the genome target microorganism; and
   (b) a mixture of four deoxynucleotide triphosphates and at least dideoxynucleotide triphosphate corresponding to one of the four deoxynucleotide triphosphates, wherein the dideoxynucleotide triphosphate is present in a mole ratio to the corresponding deoxynucleotide triphosphate of from 1:50 to 1:1000.
   (c) a polymerase enzyme which incorporates dideoxynucleotides into an extending nucleic acid polymer at a rate which is no less than 0.4 times the rate of incorporation of deoxynucleotides.

4. The kit according to claim 3, wherein the mole ratio is from 1:100 to 1:500.

5. The kit according to claim 3, wherein at least one of the primers is labeled with a fluorescent label.

6. The kit according to claim 3, wherein the primers are each labeled with a spectroscopically-distinct fluorescent label.

7. The kit according to claim 3, wherein the target microorganism is *Chlamydia trachomatis*.

8. The kit according to claim 7, wherein the first and second primers are selected from the group consisting of the oligonucleotides given by Seq. ID Nos. 1–17.

9. The kit according to claim 3, wherein the target microorganism is human immunodeficiency virus.

10. The kit according to claim 9, wherein the first and second primers are selected from the group consisting of the oligonucleotides given by Seq. ID Nos. 18–20.

11. The kit according to claim 3, wherein the target microorganism is human papilloma virus.

12. The kit according to claim 11, wherein the first and second primers are selected from the group consisting of the oligonucleotides given by Seq. ID Nos. 21–22.

* * * * *

UNITED STATES PATENT AND TRADEMARK OFFICE
CERTIFICATE OF CORRECTION

PATENT NO.    : 6,214,555 B1
DATED         : April 10, 2001
INVENTOR(S)   : Leushner et al.

It is certified that error appears in the above-identified patent and that said Letters Patent is hereby corrected as shown below:

Column 1,
Line 5, after "January 20, 1998", insert -- now US Patent No. 6,083,699, --
Line 64, delete "if" and insert -- of --

Column 2,
Line 23, after "Chlamydia" insert -- , --

Column 3,
Line 29, after "genome" insert -- of the --

Column 5,
Line 15, delete "templates" and insert -- template --

Column 6,
Line 31, delete "or" and insert -- for --
Line 62, delete "anti-biotic" and insert -- antibiotic --
Line 64, delete "micro-organism" and insert -- microorganism --

Column 7,
Line 61, delete "at" between "included" and "in"

Column 10,
Line 57, delete "EXACT SAME" and insert -- exact same --

Column 11,
Line 51, delete "patent application Serial No. 08/670,534" and insert -- Pat. No. 5,916,747 --

Column 13,
Line 2, delete "a" between "from" and "traditional"

Column 16,
Line 11, delete "has" and insert -- have --

UNITED STATES PATENT AND TRADEMARK OFFICE
CERTIFICATE OF CORRECTION

PATENT NO.   : 6,214,555 B1
DATED        : April 10, 2001
INVENTOR(S)  : Leushner et al.

It is certified that error appears in the above-identified patent and that said Letters Patent is hereby corrected as shown below:

Column 119,
Line 47, insert -- of the -- between "genome" and "target"
Line 47, delete "and"
Line 49, insert -- one -- after "least"
Line 53, delete "1:1000." and insert -- 1:1000; and --

Signed and Sealed this

Seventeenth Day of September, 2002

Attest:

JAMES E. ROGAN
*Attesting Officer*    *Director of the United States Patent and Trademark Office*